US010561575B2

(12) United States Patent
Freeman et al.

(10) Patent No.: US 10,561,575 B2
(45) Date of Patent: Feb. 18, 2020

(54) MONITORING CPR BY A WEARABLE MEDICAL DEVICE

(71) Applicant: ZOLL Medical Corporation, Chelmsford, MA (US)

(72) Inventors: Gary A. Freeman, Waltham, MA (US); Thomas E. Kaib, Irwin, PA (US); Gregory R. Frank, Mt. Lebanon, PA (US); Rachel H. Carlson, Falls Creek, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 207 days.

(21) Appl. No.: 15/463,117

(22) Filed: Mar. 20, 2017

(65) Prior Publication Data

US 2017/0281462 A1  Oct. 5, 2017

Related U.S. Application Data

(60) Provisional application No. 62/315,803, filed on Mar. 31, 2016.

(51) Int. Cl.
*A61H 31/00* (2006.01)
*G09B 5/02* (2006.01)
(Continued)

(52) U.S. Cl.
CPC ............. *A61H 31/005* (2013.01); *A61B 5/00* (2013.01); *A61N 1/0484* (2013.01);
(Continued)

(58) Field of Classification Search
CPC ...... G09B 23/30; G09B 23/28; G09B 23/202; G09B 23/32; G09B 5/04; G09B 5/06;
(Continued)

(56) References Cited

U.S. PATENT DOCUMENTS 6,272,379 B1   8/2001   Fischell et al.
6,351,671 B1   2/2002   Myklebust et al.
(Continued)

OTHER PUBLICATIONS

Cardiology Teaching Package, Jul. 20, 2015, The University of Nottingham, https://web.archive.org/web/20150720164224/https://www.nottingham.ac.uk/nursing/practice/resources/cardiology/function/chest_leads.php (Year: 2015).*
(Continued)

*Primary Examiner* — Xuan M Thai
*Assistant Examiner* — Lily M Del Valle
(74) *Attorney, Agent, or Firm* — ZOLL Medical Corporation

(57) ABSTRACT

A wearable medical device, comprising: a garment configured to be worn about a torso of a patient; one or more sensors for detecting a characteristic of a cardiopulmonary resuscitation (CPR) therapy; an output device; and a processor configured for processing information from the one or more sensors and providing, to the output device, information about the CPR therapy, wherein at least one of the one or more sensors is movably attached to the garment, the at least one sensor configured to be positioned to the center of the patient's chest prior to initiation of the CPR therapy.

30 Claims, 14 Drawing Sheets

(51) Int. Cl.
*G09B 5/04* (2006.01)
*G09B 23/28* (2006.01)
*G09B 5/06* (2006.01)
*A61N 1/04* (2006.01)
*A61B 5/00* (2006.01)
*A61N 1/39* (2006.01)

(52) U.S. Cl.
CPC .......... *A61N 1/39044* (2017.08); *G09B 5/02* (2013.01); *G09B 5/04* (2013.01); *G09B 5/06* (2013.01); *G09B 23/288* (2013.01); *A61H 2201/165* (2013.01); *A61H 2201/1614* (2013.01); *A61H 2201/1619* (2013.01); *A61H 2201/1623* (2013.01); *A61H 2201/5046* (2013.01); *A61H 2201/5061* (2013.01); *A61H 2201/5084* (2013.01); *A61H 2201/5097* (2013.01)

(58) Field of Classification Search
CPC ............... G09B 23/288; A61H 31/005; A61H 2201/1614; A61H 2201/1619; A61H 2201/1623; A61H 2201/165; A61H 2201/5046; A61H 2201/5061; A61H 2201/5084; A61H 2201/5097; A61N 1/39044; A61N 1/0484; A61B 5/00
USPC .......................................... 434/265
See application file for complete search history.

(56) References Cited

U.S. PATENT DOCUMENTS

| | | |
|---|---|---|
| 6,370,428 B1 | 4/2002 | Snyder et al. |
| 6,459,933 B1 | 10/2002 | Lurie et al. |
| 6,493,581 B2 | 12/2002 | Russell |
| 6,546,285 B1 | 4/2003 | Owen et al. |
| 6,553,257 B2 | 4/2003 | Snyder et al. |
| 6,690,969 B2 | 2/2004 | Bystrom et al. |
| 6,697,671 B1 | 2/2004 | Nova et al. |
| 6,985,771 B2 | 1/2006 | Fischell et al. |
| 6,993,386 B2 | 1/2006 | Lin et al. |
| 7,190,999 B2 | 3/2007 | Geheb et al. |
| 7,231,258 B2 | 6/2007 | Moore et al. |
| 7,272,441 B1 | 9/2007 | Chapman et al. |
| 7,976,480 B2* | 7/2011 | Grajales .................. A61B 7/04 381/67 |
| 8,734,161 B1* | 5/2014 | Centen .................. G09B 23/288 434/262 |
| 8,942,803 B1* | 1/2015 | Herken ................. A61N 1/3925 607/5 |
| 9,539,436 B2 | 1/2017 | Sullivan et al. |
| 2002/0055694 A1* | 5/2002 | Halperin ............ A61B 5/04017 601/41 |
| 2003/0233129 A1 | 12/2003 | Matos |
| 2004/0162587 A1* | 8/2004 | Hampton ............. A61H 31/005 607/5 |
| 2004/0204743 A1 | 10/2004 | McGrath et al. |
| 2005/0113885 A1 | 5/2005 | Haubrich et al. |
| 2005/0131465 A1 | 6/2005 | Freeman et al. |
| 2006/0058848 A1 | 3/2006 | Piraino et al. |
| 2006/0064136 A1 | 3/2006 | Wang |
| 2006/0116724 A1 | 6/2006 | Snyder |
| 2006/0142809 A1 | 6/2006 | Kroll et al. |
| 2006/0155336 A1 | 7/2006 | Heath |
| 2006/0270952 A1* | 11/2006 | Freeman ............. A61H 31/005 601/41 |
| 2007/0213600 A1 | 9/2007 | John et al. |
| 2007/0219588 A1* | 9/2007 | Freeman ............. A61H 31/005 607/5 |
| 2007/0299473 A1 | 12/2007 | Matos |
| 2008/0046015 A1 | 2/2008 | Freeman et al. |
| 2010/0117837 A1* | 5/2010 | Stirling ................ A61B 5/1127 340/573.1 |
| 2010/0228165 A1* | 9/2010 | Centen ................ A61H 31/004 601/41 |
| 2010/0324612 A1 | 12/2010 | Matos |
| 2011/0040217 A1* | 2/2011 | Centen ................ A61B 5/0064 601/41 |
| 2012/0010543 A1 | 1/2012 | Johnson et al. |
| 2013/0085538 A1* | 4/2013 | Volpe .................. A61N 1/3975 607/6 |
| 2013/0231711 A1 | 9/2013 | Kaib |
| 2015/0046175 A1* | 2/2015 | Jorgenson ........... A61N 1/3925 705/2 |
| 2015/0265845 A1 | 9/2015 | Sullivan et al. |

OTHER PUBLICATIONS

Compression, Nov. 9, 2015, FirstAIDWeb, https://web.archive.org/web/20151109152948/http://www.firstaidweb.com/adult4.html (Year: 2015).*

* cited by examiner

Overall Performance

| Depth | Rate | Compression Fraction | Pre-shock Pause | Post-shock Pause | Perfusion Index |
|---|---|---|---|---|---|
| 1.8 in | 118 cpm | 73% | 2.5 sec | 3.1 sec | 91% |
| [2.0-2.5 in] | [100-120 cpm] | [75%+] | [<3 sec] | [<6 sec] | [90%+] |

Minute-by-Minute CPR

| CPR Interval | Depth | Rate | Compression Fraction | Pre-shock Pause | Post-shock Pause | Perfusion Index |
|---|---|---|---|---|---|---|
| 1 | 1.9 in | 120 cpm | 78% | 2.7 | 3.0 | 90% |
| 2 | 1.2 in | 118 cpm | 70% | 2.5 | 3.3 | 94% |
| 3 | 1.5 in | 116 cpm | 70% | 2.3 | 3.8 | 86% |
| Current | 3.2 in | 110 cpm | | | | |

Fig. 13

MONITORING CPR BY A WEARABLE MEDICAL DEVICE

CROSS-REFERENCE TO RELATED APPLICATIONS

This application claims priority under 35 U.S.C. § 119(e) to U.S. Provisional Application Ser. No. 62/315,803 filed Mar. 31, 2016. All subject matter set forth in the above referenced application is hereby incorporated by reference in its entirety into the present application as if fully set forth herein.

BACKGROUND

This disclosure relates to systems and techniques for monitoring cardiopulmonary resuscitation (CPR) by a wearable medical device.

There are a wide variety of electronic and mechanical devices for monitoring and treating patients' medical conditions. In some examples, depending on the underlying medical condition being monitored or treated, medical devices such as defibrillators may be surgically implanted or connected externally to the patient. In some cases, physicians may use medical devices alone or in combination with drug therapies to treat patient medical conditions.

One of the most deadly cardiac arrhythmias is ventricular fibrillation, which occurs when normal, regular electrical impulses are replaced by irregular and rapid impulses, causing the heart muscle to stop normal contractions and to begin to quiver. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia. "Cardiac Arrest" refers generically to the medical condition of a patient in which various arrhythmias of the heart, such as ventricular fibrillation, ventricular tachycardia, pulseless electrical activity (PEA), and asystole (heart stops all electrical activity), result in the heart providing insufficient levels of blood flow to the brain and other vital organs for the support of life.

Implantable cardioverter/defibrillators (ICDs) or external defibrillators (such as manual defibrillators or automated external defibrillators (AEDs), termed "conventional external defibrillators") have significantly improved the ability to treat these otherwise life-threatening conditions. Such devices operate by applying corrective electrical pulses directly to the patient's heart. Ventricular fibrillation or ventricular tachycardia can be treated by an implanted or external defibrillator.

SUMMARY

In an aspect, a wearable medical device includes a garment configured to be worn about a torso of a patient. The wearable medical device also includes at least one ventilation sensor for detecting a characteristic of ventilations of a cardiopulmonary resuscitation (CPR) therapy. The wearable medical device also includes an output device. The wearable medical device also includes a processor configured for processing information from the at least one ventilation sensor and providing, to the output device, information about the CPR therapy.

Implementations can include one or more of the following features.

In some implementations, the wearable medical device includes at least one chest compression sensor for detecting a characteristic of chest compressions of the CPR therapy.

In some implementations, the at least one ventilation sensor and the at least one chest compression sensor is the same sensor.

In some implementations, the same sensor comprises an accelerometer.

In another aspect, a wearable medical device includes a garment configured to be worn about a torso of a patient. The wearable medical device also includes at least one chest compression sensor for measuring a characteristic of chest compressions of a CPR therapy. The at least one chest compression sensor is attached to the garment and configured on the garment such that it is positioned parasternally on the patient. The wearable medical device also includes an output device that provides feedback to a rescuer. The wearable medical device also includes a processor configured for processing information from the at least one chest compression sensor and providing, to the output device, information about the CPR therapy. The wearable medical device also includes memory connected to the processor. The wearable medical device also includes a representation of a geometry of the patient's chest used by the wearable medical device to determine one or more adjustment to be applied to motion data from the at least one chest compression sensor to enhance an accuracy of the measured characteristic of the chest compressions.

Implementations can include one or more of the following features.

In some implementations, the representation of the geometry of the patient's chest is based on generic anthropometric data from a patient population.

In some implementations, the representation of the geometry of the patient's chest is based on measurements of the patient.

In some implementations, the one or more adjustment is based on one or more of a table lookup, a linear adjustment function, and a non-linear adjustment function.

In another aspect, a wearable medical device includes a garment configured to be worn about a torso of a patient. The wearable medical device also includes one or more CPR sensors for detecting a characteristic of a CPR therapy. The wearable medical device also includes an output device. The wearable medical device also includes a processor configured for processing information from the one or more CPR sensors and providing, to the output device, information about the CPR therapy. At least one of the one or more CPR sensors is movably attached to the garment. The at least one CPR sensor is configured to be positioned to the center of the patient's chest prior to initiation of the CPR therapy.

Implementations can include one or more of the following features.

In some implementations, the at least one CPR sensor is configured to be repositioned from a location at the garment to the center of the patient's chest prior to initiation of the CPR therapy.

In some implementations, the CPR therapy includes chest compressions.

In some implementations, the CPR therapy includes ventilations.

In some implementations, the at least one CPR sensor is a chest compression sensor.

In some implementations, the chest compression sensor includes a motion sensor.

In some implementations, the motion sensor includes an accelerometer.

In some implementations, the at least one CPR sensor is stored in a compartment of the garment.

In some implementations, the at least one CPR sensor is removed from the compartment and placed at the center of the patient's chest prior to initiation of the CPR therapy.

In some implementations, the compartment includes a flap that is configured to fold away from the garment such that the at least one CPR sensor is repositioned to the center of the patient's chest when the flap is folded away from the garment.

In some implementations, the at least one CPR sensor is attached to the garment in a manner chosen to increase patient compliance with respect to wearing the garment.

In some implementations, the characteristic of the CPR therapy includes a depth of chest compressions.

In some implementations, the characteristic of the CPR therapy includes a rate of chest compressions.

In some implementations, at least one of the one or more CPR sensors includes an accelerometer.

In some implementations, at least one of the one or more CPR sensors is positioned at the side of the patient's abdomen when the garment is worn by the patient.

In some implementations, at least one of the one or more CPR sensors is positioned behind the patient when the garment is worn by the patient.

In some implementations, motion information from the CPR sensor positioned behind the patient is subtracted from motion information from the CPR sensor positioned to the center of the patient's chest.

In some implementations, the at least one CPR sensor is configured to be repositioned to a location above the patient's xiphoid process prior to initiation of the CPR therapy.

In some implementations, at least one of the one or more CPR sensors is configured to communicate wirelessly with the processor.

In some implementations, the wearable medical device includes at least one sensing electrode for sensing a cardiac arrhythmia condition of the patient, and at least one therapy electrode for delivering at least one therapeutic pulse to the patient in response to the sensed cardiac arrhythmia condition.

In some implementations, at least one of the one or more CPR sensors is integrated with the at least one therapy electrode.

In some implementations, at least one of the one or more CPR sensors is discrete from the at least one sensing electrode and the at least one therapy electrode.

In some implementations, the processor is configured to process information related to a location of a rescuer's hand during the CPR treatment.

In some implementations, the output device includes an audio output device.

In some implementations, the audio output device is configured to provide rhythmic audio indicative of a target rate of chest compressions for the CPR therapy.

In some implementations, the audio output device is configured to provide one or more verbal commands to a user administering the CPR therapy to the patient.

In some implementations, the one or more verbal commands are related to one or both of a rate of chest compressions and a depth of chest compressions of the CPR therapy being administered to the patient.

In some implementations, the output device includes a wireless transceiver for communicating with an external device having a display.

In some implementations, the display is configured to present information related to one or both of a rate of chest compressions and a depth of chest compressions of the CPR therapy being administered to the patient.

In some implementations, the display is configured to present one or more instructions to a user administering the CPR therapy to the patient.

In some implementations, the one or more instructions are related to one or both of a rate of chest compressions and a depth of chest compressions of the CPR therapy being administered to the patient.

In some implementations, the garment includes a pressure-sensitive fabric.

In another aspect, a wearable medical device includes a garment configured to be worn about a torso of a patient. The wearable medical device also includes at least two sensors for detecting a characteristic of a CPR therapy. The at least two sensors are positioned at locations at the anterior surface of the patient's chest chosen to identify a characteristic of the center of the patient's chest. The wearable medical device also includes an output device. The wearable medical device also includes a processor configured for processing information from the sensors and providing, to the output device, information about the CPR therapy. The processing includes determining information about a geometry defined by the sensors.

Implementations can include one or more of the following features.

In some implementations, the CPR therapy includes chest compressions.

In some implementations, the CPR therapy includes ventilations.

In some implementations, the characteristic of the center of the patient's chest includes a distance between the patient's sternum and the posterior of the patient.

In some implementations, the characteristic of the center of the patient's chest includes a location above the patient's xiphoid process relative to the posterior of the patient.

In some implementations, the wearable medical device includes two sensors. Determining information about the geometry defined by the sensors includes determining motion of a line defined by the two sensors.

In some implementations, the garment includes a waistband and two shoulder straps. A first sensor is positioned on the waistband and a second sensor is positioned on one of the shoulder straps.

In some implementations, the wearable medical device includes three sensors. Determining information about the geometry defined by the sensors includes determining motion of a triangular plane defined by the three sensors.

In some implementations, the garment includes a waistband and two shoulder straps. A first sensor is positioned on the waistband and a second and third sensor are positioned on the shoulder straps.

In another aspect, a wearable medical device includes a garment configured to be worn about a torso of a patient. The wearable medical device also includes one or more sensors for measuring a characteristic of a CPR therapy. The wearable medical device also includes an output device. The wearable medical device also includes a processor configured for receiving input from a measuring device that is configured for measuring information related to a geometry of the patient's chest prior to initiation of CPR. The measuring device is also configured for providing, to the output device, information about the CPR therapy based on the characteristic of the CPR therapy and the information related to the geometry of the patient's chest.

Implementations can include one or more of the following features.

In some implementations, the measuring device includes one or more accelerometers.

In some implementations, at least one of the accelerometers is configured to measure information related to acceleration in three axes.

In some implementations, at least one of the accelerometers is configured to measure information related to tilt.

In some implementations, the processor is configured to use the information related to the geometry of the patient's chest to generate a 3D representation of the patient's chest prior to initiation of CPR.

In some implementations, the measuring device is configured to measure information indicative of a location of the one or more sensors.

In some implementations, the geometry of the patient's chest includes transverse diameter of the chest.

In some implementations, the geometry of the patient's chest includes anterior-posterior diameter of the chest.

In some implementations, the geometry of the patient's chest includes contours of the chest.

In some implementations, the measuring device includes one or more cameras.

In some implementations, the one or more cameras are configured to scan a surface of the patient's chest.

In another aspect, a wearable medical device includes a garment configured to be worn about a torso of a patient. The wearable medical device also includes one or more sensing electrodes for receiving one or more cardiac signals from the patient. The wearable medical device also includes one or more CPR sensors for detecting a characteristic of a CPR therapy. The wearable medical device also includes a processor configured for determining that the patient is experiencing pulseless electrical activity (PEA) based on the received one or more cardiac signals, and providing feedback related to the CPR therapy based on the detected characteristic. The feedback is for assisting a rescuer in performing the CPR therapy.

Implementations can include one or more of the following features.

In some implementations, the CPR therapy includes chest compressions.

In some implementations, the CPR therapy includes ventilations.

In some implementations, the CPR therapy stimulates coronary circulation in the patient such that the patient's heart regains sufficient cardiac output to generate a pulse.

In some implementations, the feedback related to the CPR therapy assists the rescuer in causing a buildup of aortic pressure in the patient's heart to be optimized.

In another aspect, a wearable medical device includes a garment configured to be worn about a torso of a patient. The wearable medical device also includes one or more sensing electrodes for receiving one or more cardiac signals from the patient. The wearable medical device also includes one or more CPR sensors for detecting a characteristic of a CPR therapy. The wearable medical device also includes a processor configured for determining that the patient is experiencing fine ventricular fibrillation (VF) based on the received one or more cardiac signals, and providing feedback related to the CPR therapy based on the detected characteristic. The feedback is for assisting a rescuer in performing the CPR therapy.

Implementations can include one or more of the following features.

In some implementations, the CPR therapy includes chest compressions.

In some implementations, the CPR therapy includes ventilations.

In some implementations, the CPR therapy causes the fine VF to change to a coarse VF.

In some implementations, the feedback related to the CPR therapy assists the rescuer in causing an amplitude of the VF to be maximized.

In another aspect, a method includes receiving, by a sensing electrode of a wearable medical device, one or more cardiac signals from a patient. The method also includes detecting, by a CPR sensor of the wearable medical device, a characteristic of a CPR therapy. The method also includes determining, by a processor of the wearable medical device, that the patient is experiencing PEA based on the received one or more cardiac signals. The method also includes providing, by the processor, feedback related to the CPR therapy based on the detected characteristic. The feedback is for assisting a rescuer in performing the CPR therapy.

Implementations can include one or more of the following features.

In some implementations, the CPR therapy includes chest compressions.

In some implementations, the CPR therapy includes ventilations.

In some implementations, the CPR therapy stimulates coronary circulation in the patient such that the patient's heart regains sufficient cardiac output to generate a pulse.

In some implementations, the feedback related to the CPR therapy assists the rescuer in causing a buildup of aortic pressure in the patient's heart to be optimized.

In another aspect, a method includes receiving, by a sensing electrode of a wearable medical device, one or more cardiac signals from a patient. The method also includes detecting, by a CPR sensor of the wearable medical device, a characteristic of a CPR therapy. The method also includes determining, by a processor of the wearable medical device, that the patient is experiencing fine VF based on the received one or more cardiac signals. The method also includes providing, by the processor, feedback related to the CPR therapy based on the detected characteristic. The feedback is for assisting a rescuer in performing the CPR therapy.

Implementations can include one or more of the following features.

In some implementations, the CPR therapy includes chest compressions.

In some implementations, the CPR therapy includes ventilations.

In some implementations, the CPR therapy causes the fine VF to change to a coarse VF.

In some implementations, the feedback related to the CPR therapy assists the rescuer in causing an amplitude of the VF to be maximized.

In another aspect, a wearable medical device includes a garment configured to be worn about a torso of a patient. The wearable medical device also includes one or more CPR sensors for detecting a characteristic of a CPR therapy delivered by a rescuer. The wearable medical device also includes an output device. The wearable medical device also includes a network interface configured to communicate with a remote server. The wearable medical device also includes a processor configured for processing information from the one or more CPR sensors and providing, to the output device and the remote server, information about the CPR therapy. The output device is configured to provide, to the rescuer, an indication of a quality of the CPR therapy.

Implementations can include one or more of the following features.

In some implementations, the remote server is configured to interact with the wearable medical device to provide one or more CPR instructions to the rescuer during CPR administration.

In some implementations, the remote server is configured to interact with the wearable medical device to provide one or more CPR instructions to the rescuer based on the indication of the quality of the CPR therapy.

In some implementations, the one or more CPR instructions include applying deeper chest compressions.

In some implementations, the one or more CPR instructions include applying shallower chest compressions.

In some implementations, the one or more CPR instructions include increasing a rate of chest compressions.

In some implementations, the one or more CPR instructions include decreasing a rate of chest compressions.

In some implementations, the remote server is configured to interact with the wearable medical device to provide one or more CPR instructions to the rescuer. The one or more CPR instructions include applying ventilations.

In some implementations, the remote server is configured to interact with the wearable medical device to provide one or more CPR instructions to the rescuer. The one or more CPR instructions include ceasing the administration of the CPR therapy.

In some implementations, the remote server is configured to interact with the wearable medical device to provide one or more CPR instructions to the rescuer in real-time.

Implementations can include one or more of the following advantages.

In some implementations, the wearable medical device can be used to detect characteristics of the CPR therapy, including the rate and depths of the chest compressions, and provide appropriate feedback to the rescuer. For example, if the compressions are not deep enough, the wearable medical device can instruct the rescuer to push deeper; if the compressions are being applied too quickly, the wearable medical device can instruct the rescuer to slow down.

In some implementations, the wearable medical device is configured with CPR detection capability without sacrificing patient compliance with respect to wearing the garment. For example, patients may elect to refrain from wearing the wearable medical device if the garment is excessively burdensome and/or uncomfortable. The wearable medical device can be configured such that the sensor for detecting a CPR characteristic can be repositioned prior to initiation of CPR. That is, the sensor may be primary stored in a portion of the garment that does not affect the comfort level of the garment; prior to initiation of CPR, the sensor may be repositioned to the center of the patient's chest. In this way, the efficacy of the wearable medical device can be maximized without sacrificing patient compliance.

In some implementations, the wearable medical device may be configured to detect characteristics of the CPR without requiring a sensor to be placed at the center of the patient's chest. For example, one or more sensors positioned elsewhere on the wearable medical device may be configured to measure motion information during administration of chest compressions. The processor is configured to process the motion information from the one or more sensors to determine (e.g., infer) the motion that is occurring at the center of the patient's chest, which is typically the target location for determining depths of chest compressions. For example, a correction factor that is based on expected relative motions of various portions of the chest may be applied to the motion information to determine the depths of the chest compressions.

In some implementations, the wearable medical device may be calibrated or otherwise configured such that the correction factor can be refined for a particular patient or a particular type of patient. For example, in some implementations, the wearable medical device may consider one or more dimensions of the patient's chest to determine which correction factor should be applied and/or how a correction factors should be modified to better suit the patient. In some implementations, before administration of CPR, a measuring device can be used to measure dimensions and/or contours of the patient's chest. The measurements can be used to tailor the correction factors to the particular patient wearing the wearable medical device.

Other features and advantages of the invention will be apparent from the drawings, detailed description, and claims.

DESCRIPTION OF DRAWINGS

The accompanying drawings are not intended to be drawn to scale. In the drawings, components that are identical or nearly identical may be represented by a like numeral. For purposes of clarity, not ever component is labeled in every drawing. In the drawings:

FIG. 13 shows an example of CPR performance information.

DETAILED DESCRIPTION

Figure 1A:
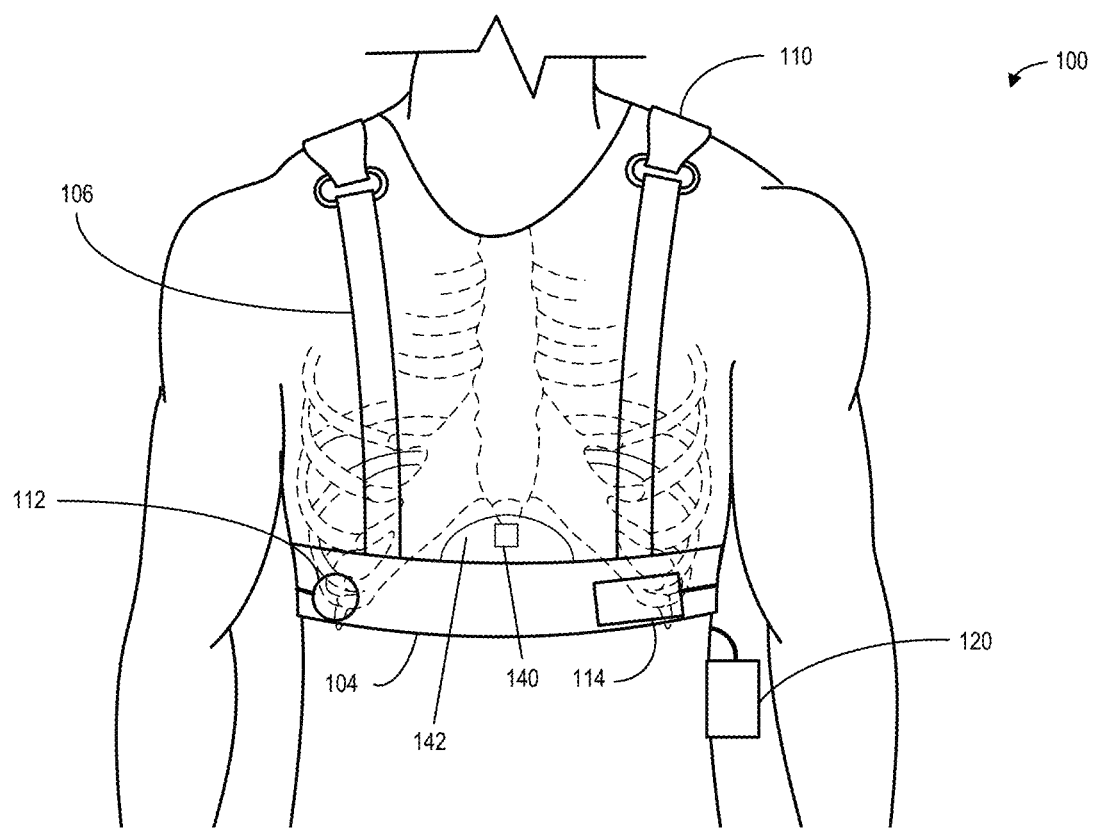
FIGS. 1A-1B show a front and back view, respectively, of an example wearable medical device that includes a garment, a medical device controller, and a sensor for detecting characteristics of a CPR therapy.

A wearable cardiac monitoring and/or treatment device can include a garment configured to be worn about a torso of a patient and one or more sensors (e.g., including one or more accelerometers) for detecting characteristics of a cardiopulmonary resuscitation (CPR) therapy administered to the patient. For example, while a user is administering CPR to the patient, an accelerometer performing the function of a chest compression sensor positioned on the patient's chest can collect motion data that is used to determine a rate and/or depth of the chest compressions being applied to the patient. Based on the determined rate and/or depth of the chest compressions, the wearable medical device can provide feedback (e.g., coaching) to assist the user in providing appropriate CPR therapy. For example, the wearable medical device may include a speaker that is configured to emit a rhythmic tone (e.g., a metronome) at a rate that matches a desired rate of chest compressions to be applied to the patient. In some implementations, the speaker may provide verbal commands to the user (e.g., "push more quickly to match tone," "push slower to match tone," "push harder," "push softer," "push deeper," "push less deep," etc.) for assisting the user in providing chest compressions at an appropriate rate and/or depth. In some implementations, instead of or in addition to the speaker, the wearable medical device may include a display for providing visual feedback to the user or can communicate with an external device, such as a tablet or smartphone, having a display that can be used for this purpose.

In some embodiments, the CPR therapy that is being measured and for which feedback is being provided is ventilator therapy (i.e. the "pulmonary" in "cardiopulmonary resuscitation"). This might be accomplished via a sound sensor, i.e. a "ventilation sensor," for measuring lung sounds. The proper rate of ventilations for victims of cardiac arrest may be 6-10 ventilations per minute. In addition, each ventilation may be delivered, ideally, in between pauses in compressions so as to minimize potentially excessive intrathoracic pressures that may lead to lung damage. For example, the chest compression sensor can detect when a pause occurs during delivery of chest compressions, and then prompt the rescuer to deliver a ventilation. The ventilation sensor can then acquire lung sounds to verify that the rescuer has delivered the ventilation, and provide feedback if the ventilation is delayed or takes too long. In some embodiments, the same accelerometer that is used for performing the function of a chest compression sensor may also be able to perform the function of a ventilation sensor. When speaking of a sensor with the generic function of measuring one or both of chest compressions and ventilation, we term the sensor a "CPR sensor." Therefore, a CPR sensor may perform either one or both of the functions of measuring chest compressions and ventilations.

In some implementations, the sensor may be configured to be repositioned from a first location on the garment to a second location at the patient's chest prior to initiation of CPR. For example, the sensor may be stored in a compartment of the garment, such as a pocket, when CPR treatment is not needed. Prior to administration of CPR, the CPR sensor may be removed from the compartment and repositioned to the center of the patient's chest (e.g., above the patient's xiphoid process). In some implementations, the sensor may be stored in a flap of the garment that is attached to a belt of the garment. The flap may be configured to assume a first position in which the flap and sensor are positioned in front of the belt, and a second position in which the flap and sensor are positioned at the center of the patient's chest. That is, the flap may be configured to fold away from the belt such that the sensor is repositioned to the center of the patient's chest. In some implementations, the sensor may be movably attached (e.g., by a hook-and-loop fastener, a snap fastener, a pivoting flap, etc.) to a location on the garment where the sensor may reside when CPR treatment is not needed.

The wearable medical device for use with the systems and techniques as disclosed herein can be configured to monitor and/or treat a patient. For example, the medical device can be configured to monitor physiological signals from the patient, and on detecting a medical event based on the monitored signals, treat the patient as needed. As described herein, a treatment sequence can include detecting a treatable medical condition, preparing the device for the treatment of the condition, providing a notification to the patient and/or others about an impending treatment, and/or delivering the treatment when certain conditions are met.

The wearable medical device may be an ambulatory device (e.g., a device that is capable of and designed for moving with the patient as the patient goes about his or her daily routine). In some examples, the wearable medical device can be configured as a wearable defibrillator, such as the LifeVest® wearable defibrillator available from ZOLL® Medical Corporation of Chelmsford, Mass. The physiological signals monitored by the device can include cardiac signals (e.g., ECG signals, heart sound signals, and other cardiac-related physiological signals) and/or one or more other signals. The wearable defibrillator may include a garment worn by the patient to which sensing and therapy electrodes are affixed for determining whether the patient may be experiencing a condition, such as a cardiac condition, and causing an appropriate treatment to be applied to the patient.

In some implementations, the wearable medical device can be configured as a cardiac monitor that is configured to transmit cardiac information in a manner similar to those employed in mobile cardiac telemetry (MCT) and/or continuous event monitoring (CEM) applications.

One of the most deadly cardiac arrhythmias is ventricular fibrillation (VF), which occurs when normal, regular electrical impulses are replaced by irregular and rapid impulses, causing the heart muscle to stop normal contractions and to begin to quiver. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia. "Cardiac Arrest" refers generically to the medical condition of a patient where various arrhythmias of the heart such as VR, ventricular tachycardia (VT), pulseless electrical activity (PEA), and asystole (heart stops all electrical activity), result in the heart providing insufficient levels of blood flow to the brain and other vital organs for the support of life.

Implantable cardioverter/defibrillators (ICDs) or external defibrillators (e.g., such as manual defibrillators and/or automated external defibrillators (AEDs), sometimes referred to as "conventional external defibrillators") have significantly improved the ability to treat these otherwise life-threatening conditions. Such devices operate by applying corrective electrical pulses directly to the patient's heart. VF and VT can be treated by an implanted or external defibrillator.

In distinction to conventional external defibrillators, some external defibrillators, termed "wearable defibrillators" (e.g., the wearable medical device), can be worn by the patient in a continuous (e.g., substantially continuous) fashion, and the patient's physiologic state can be continuously monitored, e.g., monitoring the patient's heart through one or more sensing electrodes for treatable arrhythmias and, when such is detected, the device can apply corrective electrical pulses directly to the heart through one or more therapy electrodes.

In the case of conventional external defibrillators, it is well known to those skilled in the art that adjunctive therapies in addition to defibrillation and electrical therapy are essential in many cases in order to resuscitate the cardiac arrest victim. The most typical—and sometimes the most important—adjunctive therapy is Cardiopulmonary Resuscitation (CPR) of a patient in cardiac arrest. CPR includes a collection of activities revolving around chest compressions to provide some level of blood flow to the victim's brain, heart and other vital organs both before and after defibrillation as well as some form of ventilation to the victim's lungs. The more important of these two activities is typically chest compressions. Defibrillation is a very time-sensitive therapy, and delays of even 2 minutes from onset of cardiac arrest can have a significantly deleterious effect on the patient's chance of survival. Typically, conventional external defibrillators arrive 4-15 minutes after the onset of cardiac arrest; without adequate CPR, these patients will sometimes have survival rates of less than 1-2%. Even with adequate CPR, survival rates may only reach 15-20%.

In contradistinction to conventional external defibrillators, it is known to those skilled in the art that for the case of ICDs such as implanted pacemakers and defibrillators, CPR is typically not needed for resuscitation of the cardiac arrest victim. In fact, survival rates after treatment from an ICD and without CPR will typically be in the range of 80-100%. Similar rates or survival are achieved for wearable defibrillators without the need for CPR. Thus, wearable defibrillators do not have an immediately-apparent need for CPR sensors.

It is only newly discovered by the inventors, and one of the objects of the systems and techniques described herein, that there are certain medical conditions—such as PEA or fine VF—that could be especially aided by treatment from a wearable defibrillator with one or more CPR sensors. For example, such medical conditions may benefit from the administration of CPR activities such as chest compressions. Thus, the incorporation of CPR monitoring and feedback features in a wearable defibrillator could benefit a subclass of patients who experience such medical conditions. Therefore, including one or more CPR sensors in the wearable defibrillator may have a more positive effect with respect to survival rate than previously realized, and in some cases for reasons unrelated to or in addition to the typical goals of CPR.

Pulseless electrical activity (PEA), also known as electromechanical dissociation, is a type of cardiac arrest in which a heart rhythm is observed in cardiac signals that should be producing a pulse, but it is not (e.g., an impaired pulse). When PEA is occurring, there is electrical activity in the heart, but there is insufficient cardiac output to generate a pulse and supply blood to the organs. Defibrillation is typically not an effective treatment for PEA. Rather, CPR can be performed to improve the circulation of blood in the blood vessels of the heart muscle. For example, performing chest compressions can cause aortic pressure to build up in the heart, thereby stimulating additional coronary circulation and strengthening the heart to the point that it can sufficiently beat on its own. Providing CPR feedback during such activities can ensure maximum efficacy and/or optimization.

Fine ventricular fibrillation (VF) is a type of VF in which the amplitude of the electrical activity of the heart is relatively small. Fine VF can be compared to coarse VF, in which the amplitude of the electrical activity is relatively larger. For example, prolonged VF typically results in decreasing cardiac waveform amplitude, from initial coarse VF to fine VR, and in some cases, to asystole. Such a regression occurs due to depletion of myocardial energy stores.

Coarse VF typically has a relatively high probability of successful defibrillation. On the other hand, fine VF has a significantly lower probability of defibrillation. The wearable defibrillator may determine an appropriate defibrillation treatment based on whether the patient is experiencing coarse VF or fine VF. For example, a defibrillation treatment having default characteristics may be used to treat coarse VF, whereas a defibrillation treatment having specialized characteristics may be required to treat fine VF. For situations in which the patient is experiencing fine VF, a rescuer may attempt to "coarsen up" the VF (e.g., cause the amplitude of the electrical activity to increase) by performing CPR activities such as chest compressions. Survival rates can be significantly improved by causing fine VF to revert back to coarse VF before defibrillation is administered. For example, administering chest compressions over a period of time may cause the amplitude of the VF to increase beyond a threshold (e.g., 300 mV) that classifies the VF as coarse VF. Once coarse VF is present, a default defibrillation pulse or shock may be administered. Again, providing CPR feedback to the rescuer during the administration of CPR activities can ensure maximum efficacy and/or optimization of the chest compressions, thereby increasing the amplitude of the heart's electrical activity to the fullest possible extent to reassume coarse VF.

The wearable medical device can be configured to monitor the patient for an arrhythmia condition such as bradycardia, VT, VF (both fine and coarse), PEA, and/or asystole, among others. Bradycardia, also known as bradyarrhythmia, is a slow heart rate (e.g., in some implementations, a slow resting heart rate of under 60 beats per minute in adults), which can result in fatigue, weakness, dizziness, and potentially fainting. While the detection methods and systems described hereinafter are disclosed as detecting certain medical conditions, this is not to be construed as limiting the invention. Other arrhythmias, such as, but not limited to, atrial arrhythmias such as premature atrial contractions (PACs), multifocal atrial tachycardia, atrial flutter, and atrial fibrillation, supraventricular tachycardia (SVT), junctional arrhythmias, tachycardia, junctional rhythm, junctional tachycardia, premature junctional contraction, and ventrical arrhythmias such as premature ventricular contractions (PVCs) and accelerated idioventricular rhythm, may also be detected. In some implementations (e.g., implementations in which the wearable medical device is a treatment device, such as a pacing and/or a defibrillating device), if an arrhythmia condition is detected, the wearable medical device can automatically provide a pacing or defibrillation pulse or shock to treat the condition.

After it is determined that a monitored patient may be experiencing a cardiac condition, the wearable medical device can be configured to select a treatment sequence for treating the particular condition. For example, the medical device may be configured to determine that a series of defibrillation shocks at particular intensities is appropriate for treating the particular cardiac condition. In some implementations, the device can issue up to five bi-phasic shocks if the device determines that the cardiac condition is present after each preceding shock. The device can issue more or fewer shocks to the patient as the situation may require. In some implementations, the wearable medical device may provide one or more indications (e.g., warnings or alerts) to the monitored patient or other device operator that a treatment shock is about to be delivered before it is actually delivered to the patient. On perceiving the alert, the patient or device operator may be able to instruct the wearable medical device to refrain from delivering the treatment shock. For example, the patient or the device operator may instruct the medical device to refrain from applying a treatment shock if the monitored patient is well and the wearable medical device falsely identified a cardiac event.

The wearable medical device is capable of continuous (e.g., substantially continuous) use by the patient. In some implementations, the continuous use may be substantially continuous in nature. That is, the wearable medical device may be continuously used, except for sporadic periods during which the use temporarily ceases (e.g., while the patient bathes, while the patient is refit with a new and/or a different garment, while the battery is charged/changed, while the garment is laundered, etc.). For example, such substantially continuous use as described herein may nonetheless qualify as continuous use.

The wearable medical device is also capable of extended use, and in some implementations, extended long-term use. For example, the wearable medical device can be configured to be used by the patient for hours, days, weeks, months, or even years. In some implementations, the extended use may be continuous in nature.

The use (e.g., the continuous and/or extended use) of the wearable medical device can include continuous wear by the patient, continuous attachment to the patient, and/or continuous monitoring of the patient.

The wearable medical device is configured to continuously monitor the patient for cardiac-related information (e.g., ECG information, including arrhythmia information, heart sounds, etc.) and/or non-cardiac information (e.g., blood oxygen, the patient's temperature, glucose levels, tissue fluid levels, and/or lung sounds).

The wearable medical device may carry out its monitoring in periodic or aperiodic time intervals or times. For example, the monitoring during intervals or times can be triggered by a user action or another event. For example, one or more durations between the periodic or aperiodic intervals or times can be user-configurable.

In some implementations, the patient may require another type of therapy in addition to or instead of the therapy provided by the therapy electrodes. For example, the patient may require CPR while he or she is experiencing a cardiac event, or the patient may require CPR irrespective of a cardiac event. The wearable medical device may be configured to detect characteristics of the CPR being administered to the patient by a rescuer and provide information about the CPR to the rescuer. For example, the wearable medical device may include one or more sensors (e.g., including one or more accelerometers) that are configured to detect motion that occurs during the administration of CPR. The wearable medical device can use the motion data from the sensors to determine characteristics of the CPR, such as the depth and rate of chest compressions being administered to the patient. Based on the determined CPR characteristics, the wearable medical device can provide feedback to assist the rescuer (e.g., to help the rescuer refine the treatment to achieve maximum efficacy). For example, the wearable medical device may instruct the rescuer to adjust the depth and/or rate of the chest compressions. In some implementations, the feedback may be audio, visual, and/or tactile, although other feedback methods may also be used.

Example Wearable Medical Device

Figure 1B:
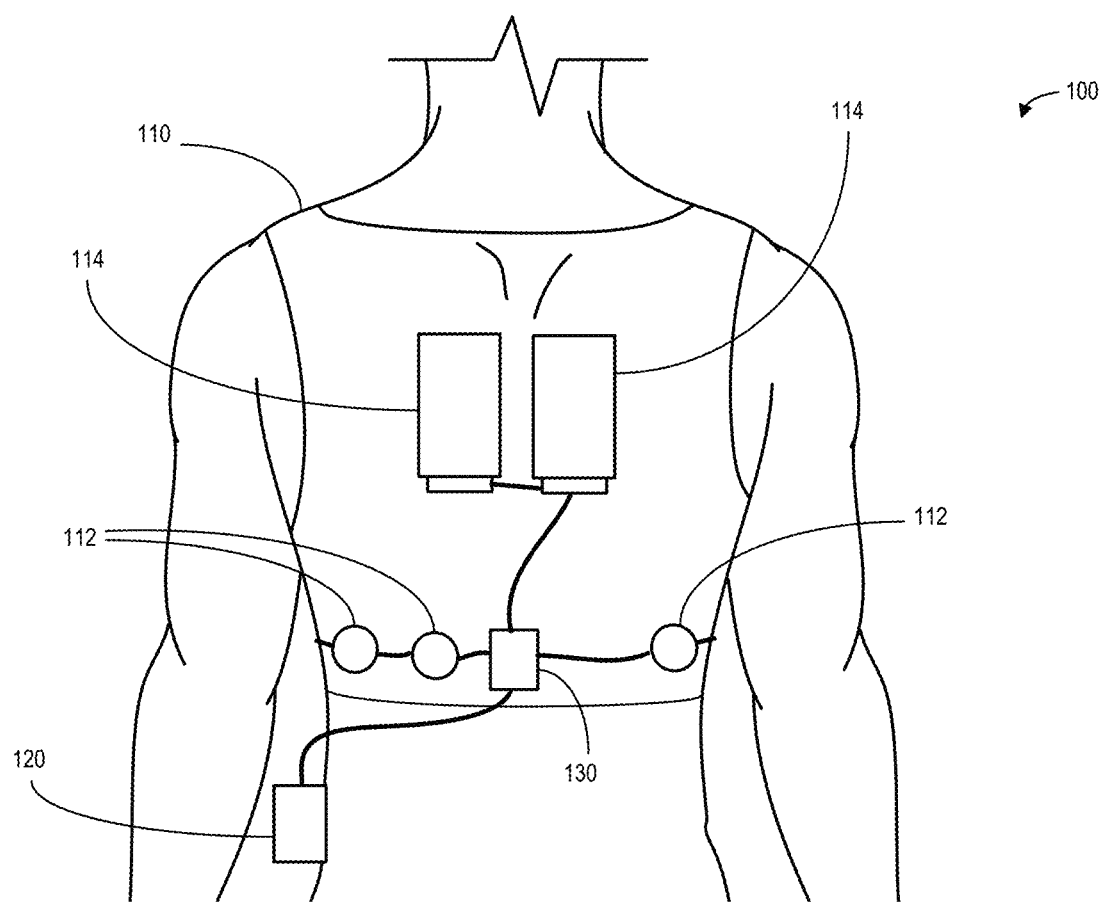

FIGS. 1A-1B show a front and back view, respectively, of an example wearable medical device 100 that is configured to provide information about a CPR therapy being administered to a patient wearing the medical device 100. The wearable medical device 100 includes a plurality of sensing electrodes 112 that can be disposed at various positions about the patient's body. In this example, one sensing electrode 112 is positioned at the front of the patient, one sensing electrode 112 is positioned at the back of the patient, and two sensing electrodes 112 are positioned at opposite sides of the back of the patient. The sensing electrodes 112 are configured to monitor the cardiac function of the patient (e.g., by monitoring one or more cardiac signals of the patient). The sensing electrodes 112 are electrically coupled to a distribution node 130 that is positioned at the back of the patient. The distribution node 130 is electrically coupled to a medical device controller 120 that can be mounted on or attached to the patient or the patient's clothing (e.g., a belt).

The wearable medical device 100 can also optionally include a plurality of therapy electrodes 114 that are electrically coupled to the medical device controller 120 through the distribution node 130. In this example, one therapy electrode 114 is positioned at the front of the patient, and two therapy electrodes 114 are positioned at the middle of the back of the patient. The therapy electrodes 114 are configured to deliver one or more therapeutic defibrillating shocks to the body of the patient if it is determined that such treatment is warranted. In some implementations, the wearable medical device 100 may be a monitoring only device that omits the therapy delivery capabilities and associated components (e.g., the therapy electrodes 114). In some implementations, various treatment components may be packaged into various modules that can be attached to or removed from the wearable medical device 100 as needed.

Components of the wearable medical device 100 are affixed to a garment 110 that can be worn by the patient (e.g., on the patient's torso). For example, the sensing electrodes 112, therapy electrodes 114, and distribution node 130 can be assembled into, integrated into, or attached to the garment 110. The garment 110 includes a waistband 104 and shoulder straps 106. In some implementations, the sensing electrodes 112 and/or the therapy electrodes 114 may be removably attached to the garment 110 (e.g., by a hook-and-loop fastener, a snap fastener, etc.). In some implementations, the garment 110 includes one or more compartments that the sensing electrodes 112 and/or the therapy electrodes 114 may be stored in. For example, the therapy electrodes 114 may be placed inside associated compartments of the garment 110 such that the therapy electrodes 114 are appropriately placed on the patient's body when the garment 110 is being worn. The compartments may include conductive fabric that is able to conduct the electrical therapy delivered to the patient.

In some cases, the medical condition experienced by the patient may be unable to be treated by one or more therapy shocks, or it may be appropriate to supplement the therapy shocks with another kind of medical treatment. For example, if the patient is experiencing an abnormal non-viable non-shockable heart rhythm or asystole (e.g., no cardiac activity), applying therapy shocks to the patient will be ineffective. In such cases, CPR may be employed to keep the patient alive (e.g., until an advanced life support team arrives). Due to the emergency nature of such situations, CPR is often delivered by laypersons who may be unfamiliar with proper CPR procedures. Thus, the wearable medical device 100 is configured to provide feedback to the rescuer to assist the rescuer in performing CPR.

According to the International Liaison Committee on Resuscitation guidelines, CPR on adults should be administered with chest compressions between 5 cm (2.0 in) and 6 cm (2.4 in) deep and at a rate of 100 to 120 compressions per minute. In addition to providing chest compressions, the rescuer may also provide breaths by exhaling into the patient's mouth or nose to push air into the patient's lungs. Current recommendations place emphasis on high-quality chest compressions. The wearable medical device 100 can provide feedback to the rescuer to ensure that the chest compressions are performed at the appropriate depth and rate.

The wearable medical device 100 includes a sensor 140 (e.g., sometimes referred to generically as a CPR sensor) that is configured to detect characteristics of a CPR therapy (e.g., chest compressions, ventilation, or both). Thus, the sensor 140 is sometimes referred to as a CPR sensor, a chest compression sensor, and/or a ventilation sensor depending on the context of use. The CPR sensor 140 may be connected to the controller 120 via one or more wires (e.g., via the distribution node 130). In some implementations, the CPR sensor 140 is configured to wirelessly communicate with the controller 120. The CPR sensor 140 may include one or more accelerometers that are configured to detect motion that occurs during the administration of CPR. The accelerometers of the CPR sensor 140 may be single or dual axis. In some implementations, the accelerometer is a solid-state ADXL202 accelerometer. The controller 120 is configured to process information (e.g., motion information) received from the CPR sensor 140 and provide information about a CPR therapy to an output device (e.g., 324 of FIG. 3) or a user interface (e.g., 308 of FIG. 3). For example, the controller 120 is configured to determine information related to the motion of the CPR sensor 140 as CPR is being administered.

The chest compression sensor 140 is configured to detect characteristics of the compressions, such as the depth and rate of chest compressions administered to the patient. For example, accelerometers incorporated into the chest compression sensor 140 may provide acceleration, velocity, and/or displacement information to the controller 120, and the controller 120 can process the information to determine the depths of the chest compressions and the rate at which the chest compressions are administered. In some implementations, acceleration readings are provided by the accelerometer at fixed time intervals (e.g., one-millisecond intervals). The depths of chest compressions are typically measured at the center of the patient's chest (e.g., at a location above the patient's xiphoid process). That is, the depth of a chest compression may be a measure of the displacement of the center of the patient's chest from an initial position (e.g., with no pressure applied to the chest) to a compressed position (e.g., when peak pressure is applied to the chest). Thus, positioning the chest compression sensor 140 above the patient's xiphoid process may provide accurate information related to the characteristics of the chest compressions, as described in more detail below.

Patient compliance is an important consideration in the design of many medical procedures and devices. Medical professionals are always trying to maximize the efficacy of a medical device without placing undue burdens on the patient. For example, if a medical device is designed for maximum efficacy but the design is very cumbersome to use, some patients may elect to not use the device due to the burden, thereby reducing the efficacy down to zero. Thus, the burden to the patient must be balanced with the medical effectiveness of the device.

In the context of the wearable medical device 100 configured to provide CPR feedback, it may be useful to position a sensor (e.g., the chest compression sensor 140) at the center of the patient's chest, such as above the patient's xiphoid process, to provide motion information that is especially relevant for determining chest compression characteristics. However, doing so may require a portion of the garment 110 to be constantly positioned at this location. That is, the garment 110 may require a strap that wraps around the center of the patient's chest. Considering that the wearable medical device 100 is configured for moving with the patient as the patient goes about his or her daily routine, and in some cases may be continuously (e.g., substantially continuously) worn for hours, days, weeks, months, or even years, such a burden may result in decreased compliance. In other words, the patient may elect to simply not wear the medical device 100 because it is uncomfortable. While such an implementation is within the scope of this disclosure, other configurations may provide sufficient function without creating an undue burden on the patient.

In some implementations, the chest compression sensor 140 is movably attached to the garment 110. The chest compression sensor 140 is configured to be repositioned to the center of the patient's chest prior to initiation of the CPR therapy. Thus, when CPR is not being delivered (e.g., a significant majority of the time that the patient is wearing the medical device 100), the patient does not experience the potentially cumbersome and/or uncomfortable placement of the chest compression sensor 140 at the center of his or her chest. In this way, neither efficacy nor compliance is sacrificed.

In the example shown in FIGS. 1A-1B, the chest compression sensor 140 is stored in a compartment of the garment 110. The compartment may be a flap 142 that is attached to the waistband 104 of the garment 110 (e.g., at a central portion of the waistband 104) and configured to fold away from the garment 104. When the wearable medical device 100 is properly worn by the patient, the waistband 104 may be positioned over the bottom few ribs and just below the xiphoid process of the patient. When the flap 142 is folded away from the garment 110 (e.g., prior to initiation of CPR), the flap 142 and the chest compression sensor 140 are positioned at a location above the patient's xiphoid process. In this way, the chest compression sensor 140 may be in proper position for providing accurate CPR feedback information during administration of the CPR therapy. In some implementations, the chest compression sensor 140 may be attached to the garment 110 in a manner chosen to increase patient compliance with respect to wearing the garment 110.

While FIGS. 1A-1B show four sensing electrodes 112 and three therapy electrodes 114, any number of sensing electrodes 112 and/or therapy electrodes 114 may be provided and disposed at various locations about the patient's body. Similarly, while only one chest compression sensor 140 is shown, the wearable medical device 100 may include additional chest compression sensors, as described in more detail below.

Figure 2A:
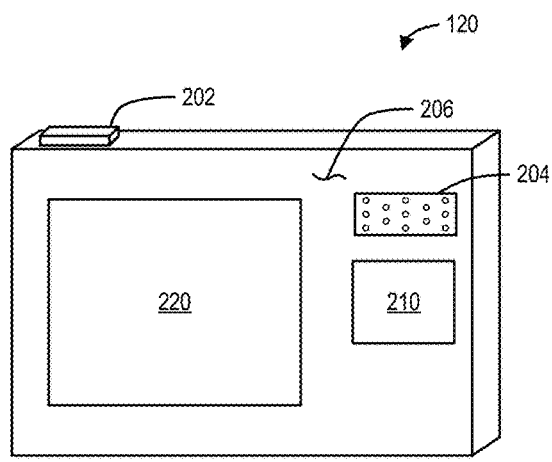
FIGS. 2A-2B shows an example of the medical device controller of FIGS. 1A-1B.
Figure 2B:
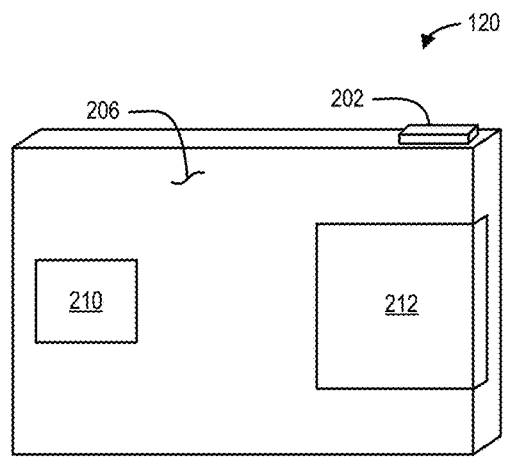

FIGS. 2A-2B show an example of the medical device controller 120 of FIGS. 1A-1B. The controller 120 may be powered by a battery 212 (e.g., a rechargeable battery) that can be removable from a housing 206 of the controller 120 to allow for recharging. The controller 120 includes a user interface such as a touch screen 220 that can provide information (e.g., information related to a CPR treatment) to the patient and/or a rescuer, as described in more detail below. The patient can interact with the touch screen 220 in order to communicate with and control the wearable medical device 100. The controller 120 also includes a speaker 230 that can provide information to the patient and/or a rescuer.

The controller 120 also includes a port 202 to which the distribution node 130 can be attached and response buttons 210 that the patient can interact with in order to cause the wearable medical device 100 to withhold delivery of a treatment (e.g., if the patient is well and the wearable medical device 100 falsely identified a cardiac event).

Figure 3:
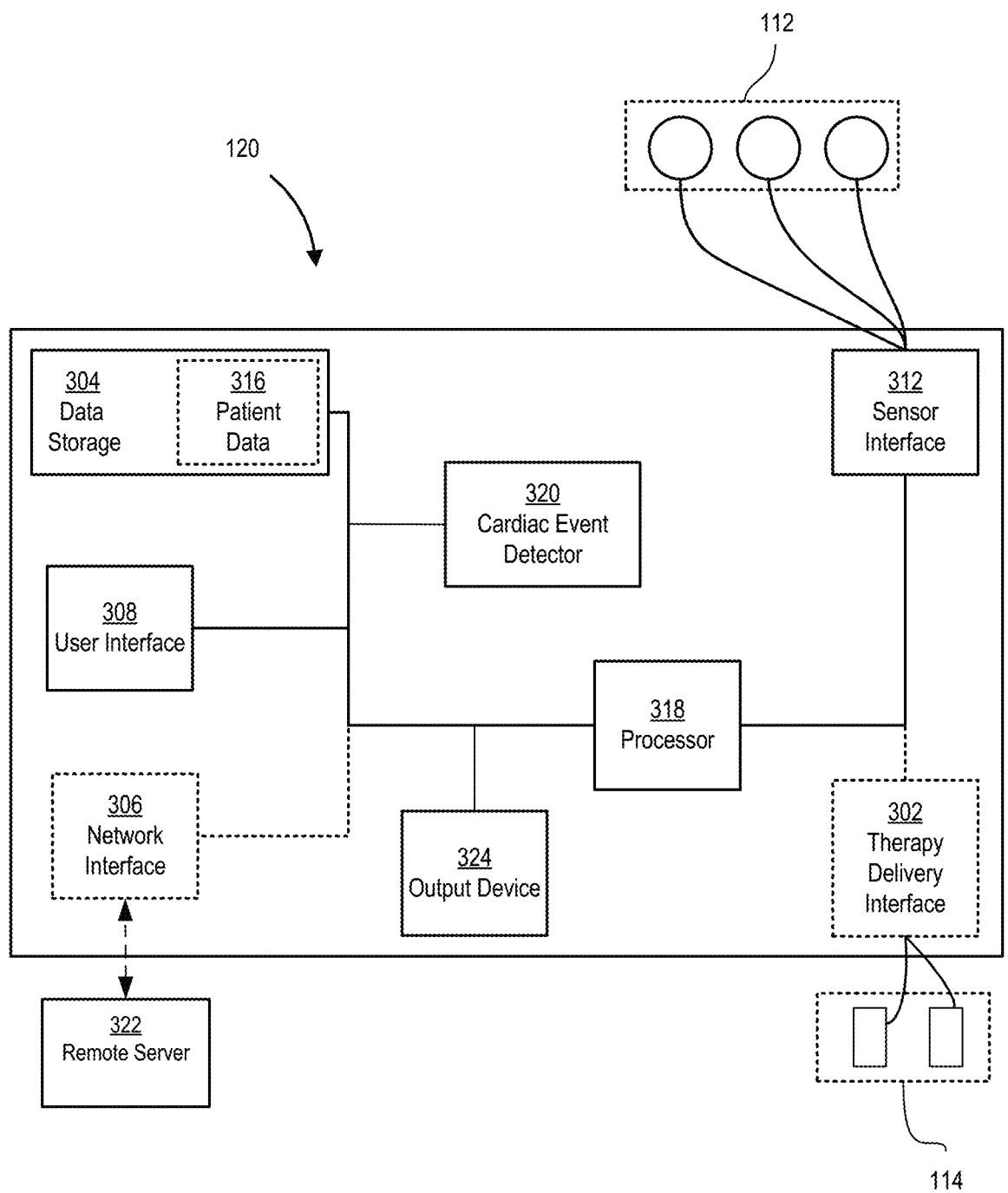
FIG. 3 shows a schematic of an example of the medical device controller.

FIG. 3 shows a schematic of an example of the medical device controller 120 of FIGS. 1A-1B and 2A-2B. The controller 120 includes a processor 318, a cardiac event detector 320, an output device 324, a patient sensor interface 312, an optional therapy delivery interface 302, data storage 304 (which may include patient data storage 316), an optional network interface 306, and a user interface 308 (e.g., including the touch screen 220 shown in FIG. 2A). In some implementations, the user interface 308 may include the output device 324. That is, the user interface 308 and the output device 324 may be the same component of the controller 120. The patient sensor interface 312 is coupled to the patient sensing electrodes 112 via the distribution node 130, and the therapy delivery interface 302 (if included) is coupled to the patient therapy or therapy electrodes 114 via the distribution node 130. The patient sensor interface 312 and the therapy delivery interface 302 implement a variety of coupling and communication techniques for facilitating the exchange of data between the patient electrodes 112, 114 and the controller 120.

In some implementations, the processor 318 can perform a series of instructions that control the operation of the other components of the controller 120. The cardiac event detector 320 is configured to monitor the cardiac activity of the patient and identify cardiac events experienced by the patient based on received cardiac signals. In some examples, the cardiac event detector 320 can access patient baseline information in the form of templates (e.g., which may be stored in the data storage 304 as patient data 316) that can assist the cardiac event detector 320 in identifying cardiac events experienced by the patient, as described above. The baseline ECG recordings may be obtained during initial setup of the device.

In some examples, the network interface 306 can facilitate the communication of information between the controller 120 and one or more other devices or entities over a communications network via either a wired or wireless connection. In some examples, the network interface 306 is configured to communicate with a server (e.g., a remote server 322). In some implementations, the remote server 322 is a remote medical server that can be accessed by a medical service provider, such as a doctor, to obtain information related to the patient being monitored and/or treated by the wearable medical device 100. In this way, the medical service provider can remotely monitor the patient's medical condition and take appropriate action. After a treatment is delivered, a status and results of such treatment may be transmitted to the remote server 322. The transmissions may occur continuously, at fixed intervals, or upon occurrences of particular events, among others. In some implementations, the communication may occur via a telephone network or a cellular network (e.g., 2G, 3G, 4G), among others.

As mentioned above, in some implementations, the wearable medical device 100 is capable of and designed for being worn by a patient who is at risk of developing cardiac problems, but who does not yet meet criteria to be outfitted with a medical device that includes a treatment component (e.g., a defibrillator). In such implementations, the controller 120 may omit the treatment components, including the therapy delivery interface 302 and the therapy electrodes 114. A wearable medical device 100 that does not include treatment components is sometimes referred to as a monitor (e.g., a cardiac monitor). The cardiac monitor may be prescribed so that continuous and/or event-based data can be sent from the cardiac monitor to a server (e.g., the remote server 322). A caregiver can access the data from the remote server 322 and determine whether the patient is experiencing or has experienced a cardiac problem. In some implementations, after determining that the patient is experiencing a cardiac problem, the caregiver may instruct the patient to begin wearing a medical device with treatment capabilities.

In addition to controlling the cardiac monitoring and the delivery of therapeutic shocks by the wearable medical device 100, processor 318 is also configured to process information from the chest compression sensor 140 to determine one or more characteristics of a CPR therapy administered to the patient. For example, accelerometers incorporated into the chest compression sensor 140 may provide acceleration, velocity, and/or displacement information to the processor 318, and the processor 318 can process such motion information to determine the depths and rate of the chest compressions being administered. The processor 318 can determine whether the depths and/or the rates of the chest compressions satisfy predetermined criteria, including determining whether the depths and/or rates are within predetermined ranges, and cause the wearable medical device 100 to respond accordingly.

Figure 4:
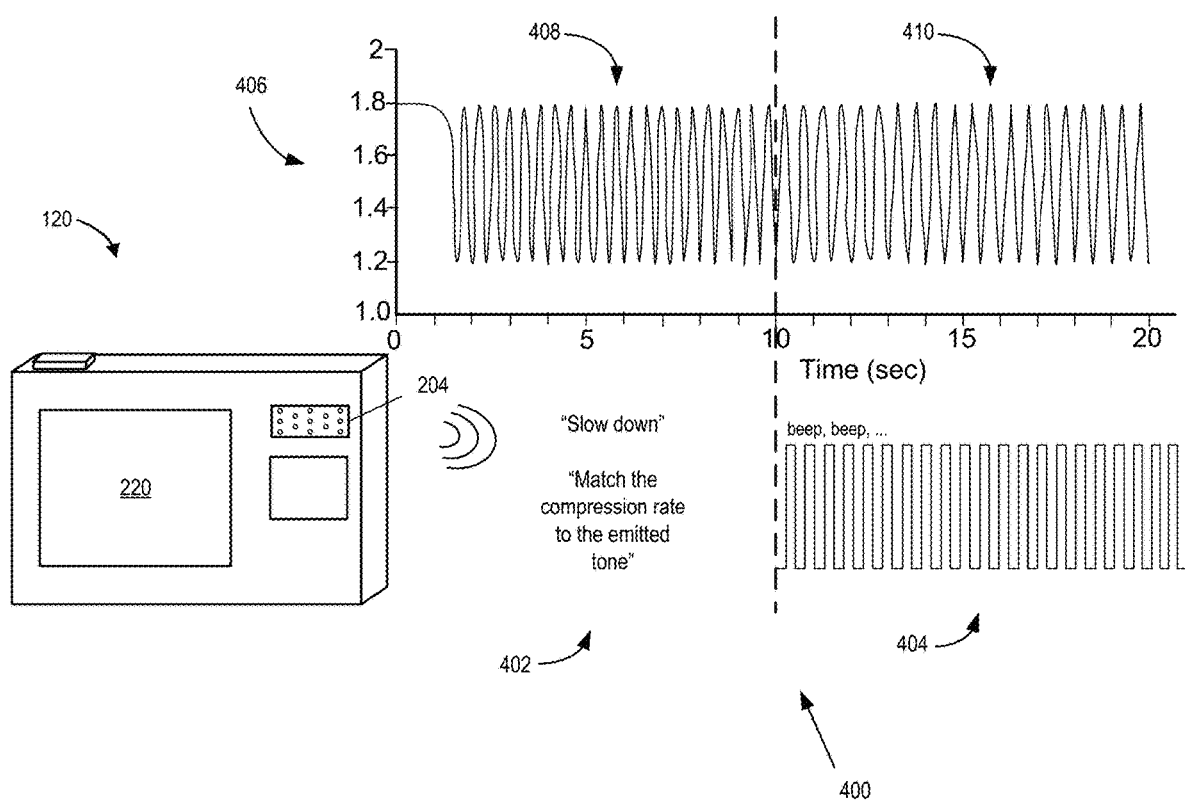
FIGS. 4 and 5 depicts CPR feedback information provided by the medical device controller.

FIG. 4 shows a visual depiction of audio CPR feedback information 400 that can be provided by the medical device controller 120 in response to a CPR therapy administered to the patient. In some implementations, the wearable medical device 100 may provide an initial indication that CPR should be administered to the patient using the output device (324 of FIG. 3). The output device 324 may include the touch screen 220 and/or the speaker 204 of FIGS. 2A-2B. For example, the wearable medical device 100 may provide an initial indication that CPR should be administered by providing a message via the touch screen 220 or by emitting a verbal command via the speaker 204. The wearable medical device 100 may instruct the rescuer to position the chest compression sensor 140 to the center of the patient's chest. For example, the rescuer may be instructed to fold the flap 142 in which the chest compression sensor 140 is stored away from the garment such that the flap 142 is repositioned to the center of the patient's chest, or the rescuer may be instructed to remove the chest compression sensor 140 from the compartment and reposition the chest compression sensor 140 to the center of the patient's chest.

Once the chest compression sensor 140 is properly positioned, the rescuer may be instructed to begin chest compressions. In some implementations, the wearable medical device 100 may provide additional information related to how the chest compressions should be performed. For example, the wearable medical device 100 may instruct the rescuer to place his or her hands at the center of the patient's chest and push at a rate of approximately 120 compressions per minute. In some implementations, the wearable medical device 100 may also instruct the rescuer to strive for applying compressions having depths of approximately 2.0 to 2.5 inches; however, specific initial instructions related to the depths of chest compressions may be of limited help to a layperson, and are sometimes initially omitted.

As CPR is administered, the chest compression sensor 140 determines characteristics related to the CPR therapy and provides motion information to the processor 318. The motion information may include data related to the acceleration, velocity, and/or displacement of the chest compression sensor 140. The processor 318 processes the data to determine the rate and depths of the compressions that are being delivered to the patient. A visual depiction of the motion data 406 shows the motion of the chest compression sensor 140 as a function of time. The motion data may comprise acceleration data, velocity data, and/or displacement data. The visual depiction of the motion data 406 includes a first portion 408 during which the rate and depths of the chest compressions are initially determined. The first portion 408 of the motion data indicates that the actual rate of the compressions being administered is approximately 150 compressions per minute. According to medical guidelines, such a compression rate is too fast.

The processor 318 is configured to instruct the speaker 204 of the controller 120 to emit a verbal command 402 instructing the rescuer to "slow down." The verbal command 402 may also include an instruction to "match the compression rate to the emitted tone." The speaker 204 may then emit a periodic tone 404 (e.g., a metronome) that is emitted at a rate that corresponds to the desired rate of the chest compressions. In this way, the rescuer has an audible cue indicating the proper chest compression rate. Utilizing such audio feedback allows the rescuer to focus his or her attention to providing treatment to the patient without requiring the rescuer to look away.

The visual depiction of the motion data 406 includes a second portion 410 that indicates the detected rate of the chest compressions after the "slow down" instruction was given. The second portion 410 indicates that the rescuer has successfully slowed the compression down to a rate of approximately 120 compressions per minute, which falls within acceptable medical guidelines. However, if the rate of compressions is still too fast, the speaker 204 may emit another verbal command 402 to "slow down" along with a reminder to "match the compression rate to the emitted tone." In some implementations, the second message may be provided with increased volume to capture the rescuer's attention and/or to indicate that the rescuer has not satisfied the initial verbal command.

If after emitting the verbal command 402 the compressions have slowed down below an acceptable threshold (e.g., below 100 compressions per minute), the speaker 204 may instruct the rescuer to "speed up" and remind the rescuer to "match the compression rate to the emitted tone."

While the CPR feedback is shown as a visual depiction of audio CPR feedback information 400, compression rate feedback can be provided in other ways. For example, information similar to the visual depiction may be provided on the touch screen 220 of the controller 120 in addition to or instead of the audio CPR feedback.

The motion data may also include information used by the processor 318 to determine the depths of the chest compressions being administered. For example, the processor 318 may use displacement data provided by the chest compression sensor 140 to determine the compression depths. Based on the determined depths of the compressions, the processor 318 is configured to instruct the speaker 204 to emit another verbal command instructing the rescuer to "push harder" or "push deeper," or "push softer" or "push less deep." The degree by which the rescuer should push softer/less deep or harder/deeper may be indicated by the language of the verbal command. For example, the verbal commands may include "push much softer" or "push much less deep," or "push much harder" or "push much deeper," among others. In some implementations, the degree by which the rescuer should push softer/less deep or harder/deeper may be indicated in other ways. For example, the volume of the verbal command may be proportional to the depths of the compressions that the rescuer should strive for (e.g., a very loud "push deeper" command may indicate that the rescuer should push much deeper).

Figure 5:
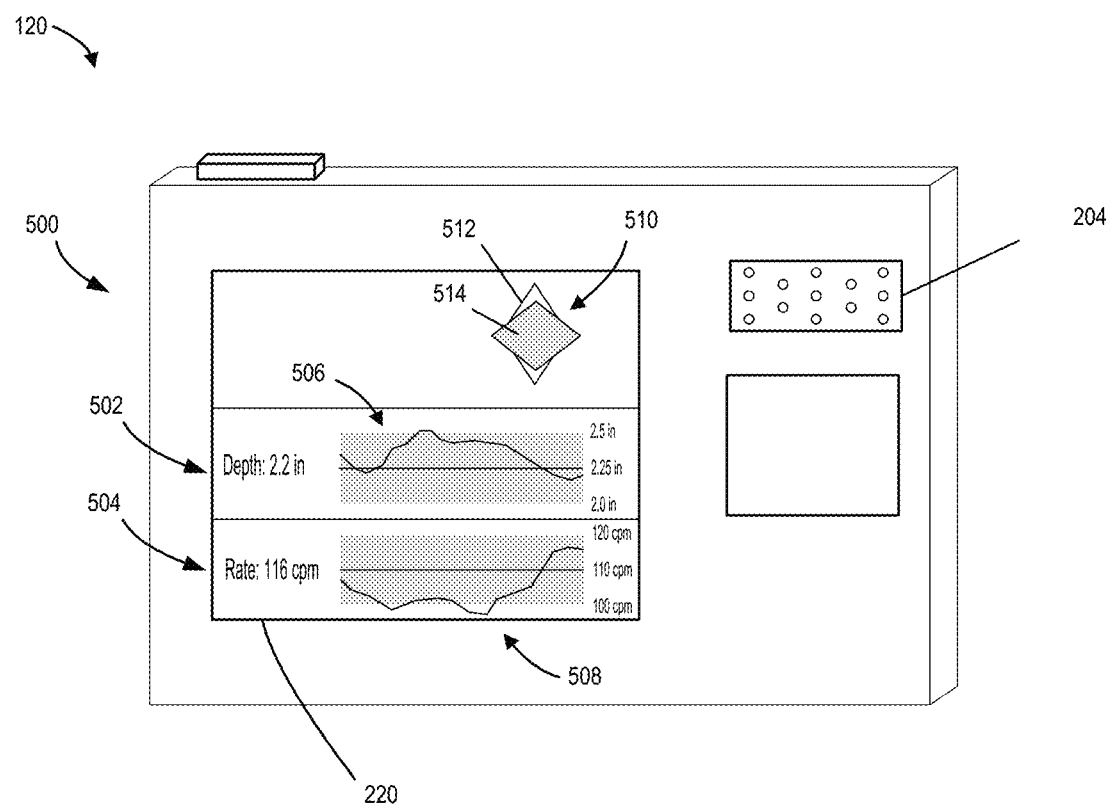

In some implementations, conveying information related to the desired depths of the chest compressions may be accomplished by visual indicators. FIG. 5 shows an example of visual CPR feedback information 500 that can be provided by the medical device controller 120 in response to a CPR therapy administered to the patient. In a manner similar to that described above with respect to FIG. 4, the rescuer may initially be instructed to position the chest compression sensor 140 to the center of the patient's chest and begin chest compressions. As CPR is administered, the CPR sensor 140 determines characteristics related to the CPR therapy and provides motion information, heart sound information, and/or lung sound information to the processor 318. The processor 318 is configured to cause the touch screen 220 to present the depth 502 and rate 504 of chest compressions currently being administered to the patient. The compression depth 502 and/or rate 504 may be presented as an instantaneous measurement. In some implementations, the depth and/or rate 504 is presented as an average of the last few depth and/or rate measurements as determined by the processor 318.

In some implementations, the touch screen 220 is also configured to present a depth graph 506 and a rate graph 508 that show the depth/rate trends of the administered chest compressions. Such graphs 506, 508 can provide relative information to the rescuer to allow the rescuer to put the current compression depth and/or rate into context. The depth graph 506 may present the depths of compressions administered over a fixed period of time (e.g., over the past 10 seconds). In this way, the rescuer can visualize how adjustments to the compression effort applied to the patient's chest have manifested in terms of the compression depths detected by the chest compression sensor 140. The depth graph 506 may include a shaded portion that indicates a target zone within which the actual depths of the compressions should reside. The target compression depth may be 2.25 inches, which may be approximately halfway between the maximum target compression depth of 2.5 inches and the minimum target compression depth of 2.0 inches. In some implementations, the shaded portion may change color based on whether the depths of compressions currently being administered is within the target range. For example, if the current compression depths are 2.2 inches, as shown in FIG. 5, the shaded portion may be green; if the compression depths were to rise above 2.5 inches or fall below 2.0 inches, the shaded portion may turn red. In some implementations, the intensity of the color of the shaded portion may correspond to the degree of compliance with the target compression depth. For example, if the compression depths are exactly 2.25 inches, the shaded portion may be bright green; as the compression depths move away from the ideal target depth, the bright green may change to a faded green; as the compression depths approach the upper or lower limit, the faded green may begin to turn to faded red; and when the compression depths fall outside of the target zone, the faded red may change to bright red.

Similarly, the rate graph 508 may present the rate of compressions administered over a fixed period of time (e.g., over the past 10 seconds). In this way, the rescuer can visualize how adjustments to the rate of the compressions applied to the patient's chest have manifested in terms of the compression rate detected by the chest compression sensor 140. The rate graph 508 may include a shaded portion that indicates a target zone within which the actual rate of the compressions should reside. The target compression rate may be 110 compressions per minute, which may be approximately halfway between the maximum target compression rate of 120 compressions per minutes and the minimum target compression rate of 100 compressions per minute. In some implementations, the shaded portion may change color based on whether the current compression rate is within the target range. For example, if the current compression rate is 116 compressions per minute, as shown in FIG. 5, the shaded portion may be green; if the compression rate were to rise above 120 compressions per minute or fall below 100 compressions per minute, the shaded portion may turn red. In some implementations, the intensity of the color of the shaded portion may correspond to the degree of compliance with the target compression rate. For example, if the compression rate is exactly 110 compressions per minute, the shaded portion may be bright green; as the compression rate move away from the ideal target rate, the bright green may change to a faded green; as the compression rate approach the upper or lower limit, the faded green may begin to turn to faded red; and when the compression rate falls outside of the target zone, the faded red may change to bright red.

In some implementations, the touch screen 220 is also configured to present an adaptable shape that indicates both the depths and rate of compressions being administered. The adaptable shape is sometimes referred to as a perfusion performance indicator (PPI) 510. The PPI 510 may be presented instead of or in addition to the depth 502, rate 504, depth graph 506, and/or rate graph 508. The PPI 510 has an outer border 512 having a shape (e.g., a diamond) that is shaded 514 (e.g., with color) over time. The amount of the shading 514 that fills the outer border 512 (e.g., the fill amount) provides feedback about both the rate and depth of the compressions being administered. For example, when CPR is being performed at or near ideal parameters, the shading 514 may fill the entire outer border 512; as the rate and/or depth decreases toward the lowest acceptable limits, the amount of fill lessens; as the rate and/or depth increases toward the highest acceptable limits, the amount of fill increases beyond the outer border 512 of the PPI 510. In some implementations, the outer border 512 corresponds to the ideal target compression rate and depth. The PPI 510 can provide a concise visual indication of the quality of the CPR such that the rescuer can aim to keep the PPI 510 completely filled.

In some implementations, the PPI 510 includes two axes—a vertical axis and a horizontal axis. The vertical axis may correspond to the depth of chest compressions, and the horizontal axis may correspond to the rate of chest compressions. For example, when the depth of chest compressions decreases toward the lower acceptable limit, the shading 514 of the PPI 510 in the vertical direction may be relatively small. Similarly, when the rate of chest compressions decreases toward the lower acceptable limit, the shading 514 of the PPI 510 in the horizontal direction may be relatively small. In the example shown in FIG. 5, the depths of the compressions are slightly below the ideal target value and the rate of the compressions is above the ideal target value; accordingly, the shading 514 of the PPI 510 has a short, wide diamond shape. Such a shading 514 indicates that the rescuer should slightly increase the depths of the compressions and reduce the rate of the compressions.

In some implementations, the color of the shading 514 may correspond to the compliance of the compression depths and/or rate. For example, if one or both of the depths of compressions and the rate of compressions falls below the corresponding lowest acceptable limit or the corresponding highest acceptable limit, the shading 514 may have a red color; when both of the depths of compressions and the rate of compressions are within the corresponding target ranges, the shading 514 may have a yellow color (e.g., indicating that the depths and rates are within the target range but there exists room for improvement) or a green color (e.g., indicating that the depths and rates are at or near the ideal target values).

In some implementations, the wearable medical device 100 may include a wireless transceiver configured to communicate with one or more external devices. For example, output device 324 may include a wireless transceiver, or the output device 324 may be configured to interact with the network interface (306 of FIG. 3) to communicate with an external device having a display. In some implementations, rather than or in addition to the touch screen 220 of the controller 120 presenting the information described above with reference to FIGS. 4 and 5, the controller 120 may cause the external device to present information related to the CPR therapy and/or feedback information. In some implementations, the controller 120 is configured to wirelessly communicate with a mobile computing device such as a tablet, smartphone, or laptop, among others. In some implementations, the network interface (306 of FIGS. 3 and 12) and/or the remote server (322 of FIGS. 3 and 12) are configured to interact with an external device in order to provide CPR information and/or feedback information to one or more remote entities. In this way, remote medical personnel can observe information related to the therapy being administered to the patient.

Figure 12:
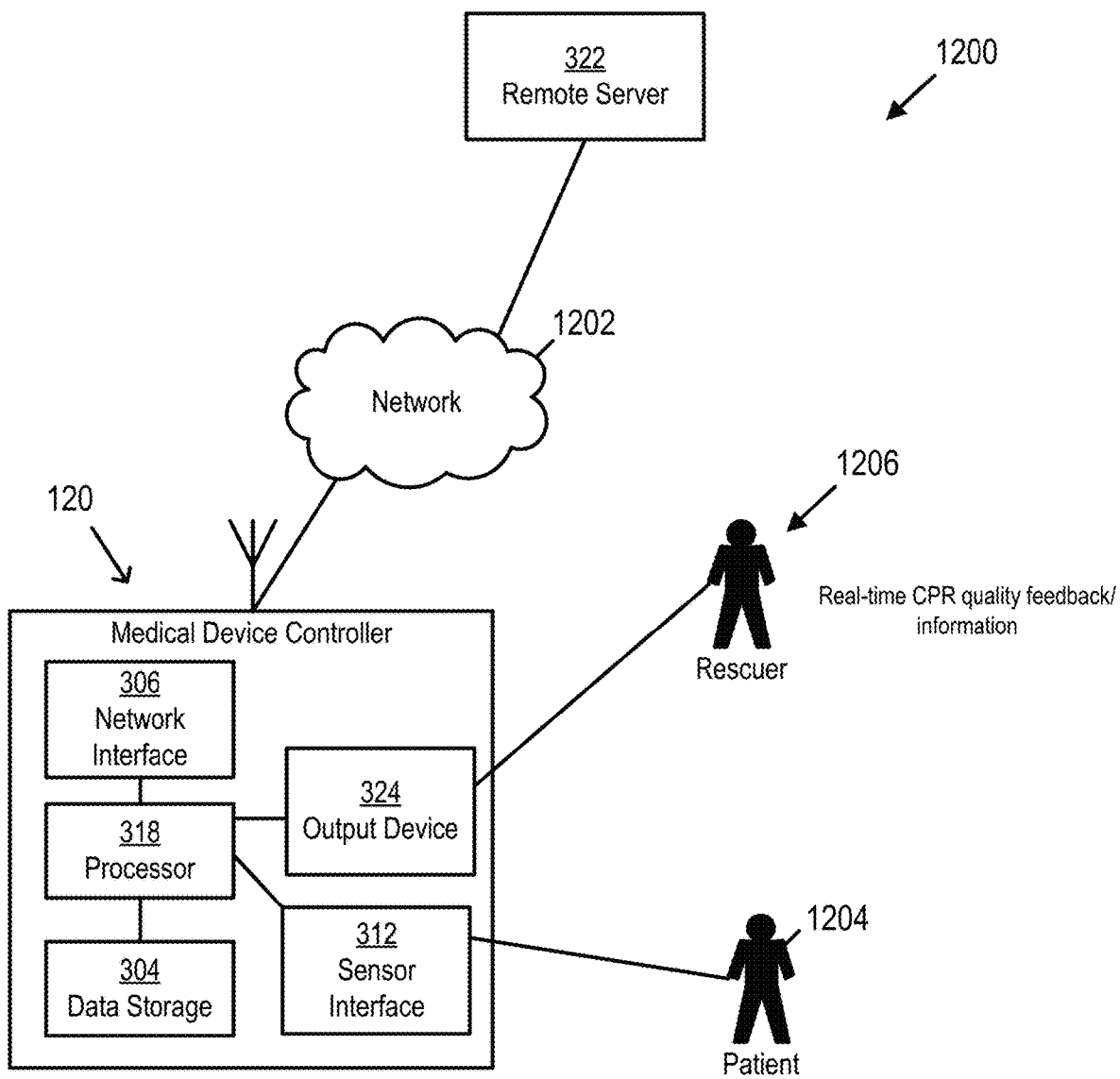
FIG. 12 shows an example of a system in which the medical device controller is configured to communicate with a remote server.

In some implementations, the controller 120 is configured to communicate with the remote server 322, thereby allowing a remote entity to interact with the controller 120. FIG. 12 shows an example of a system 1200 in which the controller 120 is configured to communicate with the remote server 322 via a network 1202 (e.g., a wireless network). For example, instead of or in addition to providing information about the CPR therapy to the output device 324 based on processing and/or computations that take place at the controller 120, the processor 318 may be configured to provide information about the CPR therapy to the remote server 322. The information may then be examined by the remote entity at the remote server 322 (e.g., via a computing device such as a computer, laptop, tablet, or smartphone, among others). The remote entity may be a caregiver such as a doctor, nurse, or other medical professional.

The caregiver can access the information about the CPR therapy at the remote server 322 and provide appropriate feedback in response. For example, the remote server 322 may receive information from the one or more CPR sensors related to ventilations, a rate of chest compressions, and/or a depth of chest compressions being applied to a patient 1204 by a rescuer 1206. Based on the information, the caregiver can determine a quality of the CPR therapy that is being administered by the rescuer 1206. The caregiver may then provide an indication of the quality of the CPR therapy to the controller 120 via the network 1202, and the controller 120 can provide the indication via the output device 324 to be observed by the rescuer 1206. In this way, real-time CPR feedback can be provided to the rescuer 1206 by an actual caregiver who may have a relatively greater level of medical expertise.

FIG. 13 shows an example of information related to the performance of CPR being administered. The information may be provided to the caregiver at the remote server 322 to indicate the overall quality of the CPR being administered to the patient 1204 by the rescuer 1206. In some examples, the information is presented on a computing device in communication with the remote server 322. The presentation of information in this example is split into two portions—a top portion that shows averaged performance over an entire incident, and a bottom portion that shows the performance average over each of a number of past CPR intervals, with display of current compression depth and rate displayed under the second portion. In addition to the compression depth and rate information largely described herein, the CPR performance information can include an indication of a compression fraction, a pre-shock pause, a post-shock pause, and a perfusion index. The information may be based on data received at the remote server 322 from the one or more CPR sensors.

In this example, the caregiver sees that the rescuer 1206 is currently administering chest compressions at a depth of 3.2 inches and at a rate of 110 compressions per minute. Based on this information, the caregiver may determine that the depths of the compressions are too deep, but the rate of the compressions is just right. In response, the caregiver may provide one or more CPR instructions to the rescuer 1206 at the remote server 322 via the network 1202. For example, the caregiver may input one or more CPR instructions into the computing device and cause the CPR instruction to be transmitted to the controller 120 via the network 1202. In this example, the instruction may instruct the rescuer 1206 to apply shallower chest compressions and maintain the current rate of the compressions.

The rescuer 1206 may adjust the administration of the CPR therapy based on the one or more CPR instructions provided by the caregiver. The caregiver may again access the information related to the CPR therapy at the remote server 322 to determine whether the CPR therapy is now being administered appropriately. If further adjustment is necessary, the caregiver may provide one or more additional CPR instructions. In this way, the CPR therapy can be refined with real-time evaluation from the caregiver until appropriate CPR characteristics are attained and/or maintained. The real-time CPR evaluation may be limited only by the processing and/or transmitting capabilities of the controller 120, the network 1202, and/or the remote server 322.

In some implementations, the CPR instructions may be directed to other aspects of the CPR therapy. For example, the CPR instruction may direct the rescuer to apply deeper chest compressions or to increase/decrease the compression rate. In some implementations, the instruction may direct the rescuer 1206 to apply ventilations to the patient 1204 or adjust characteristics of ventilations being applied to the patient 1204. In some implementations, the instruction may direct the rescuer 1206 to cease the administration of the CPR therapy altogether. The particular instructions that the caregiver remotely provides to the rescuer 1206 may be based on the totality of the CPR information at the remote server 322, including the information related to the overall performance of the CPR and the information related to past CPR intervals. In this way, the medically-qualified caregiver has the freedom to make on-demand judgment calls in real-time as to the appropriate adjustments to the CPR that should be applied for maximum efficacy, thereby providing an additional aspect of personalization over implementations in which the controller 120 determines the adjustments according to predetermined rules.

The one or more CPR instructions remotely provided by the caregiver may be provided via the output device 324 (e.g., including the touch screen 220 and/or the speaker 204 of the controller 120). For example, the caregiver's CPR instructions may be presented as messages on the touch screen 220 and/or as a spoken instructions emitted from the speaker 204. In some implementations, the caregiver may provide real-time CPR feedback in a manner similar to that described above with respect to the perfusion performance indicator (PPI) 510 of FIG. 5. In some implementations, CPR instructions provided by the caregiver may automatically override instructions automatically determined at the controller 120 itself. For example, if the controller 120 determines that a remote caregiver is actively monitoring the CPR therapy and providing instructions in real-time, the controller 120 may refrain from providing its own instructions so long as the caregiver continues monitoring. In some implementations, the controller 120 may continue to provide its own instructions, and the caregiver's instructions may serve to supplement those.

In some implementations, some or all of the processing of the information from the CPR sensor may be performed at the remote server 322. For example, the one or more CPR sensors may provide raw and/or minimally processed data to the remote server 322 via the network 1202. The remote server 322 may process the data and provide, to the controller 120, information about the CPR therapy. For example, the one or more CPR sensors may provide raw accelerometer data to the remote server 322, and the remote server 322 may determine the rate and depth of chest compressions based on the data. The remote server 322 may also determine appropriate feedback for refining the CPR therapy based on the determined characteristics. Thus, remote computing systems having enhanced processing capabilities may be utilized without requiring the controller 120 to support extensive processing locally.

In some implementations, the indication of the quality of the CPR may be an indication of the overall quality of the CPR therapy. For example, the indication of the quality of the CPR may be based on a combination of information related to chest compression depth, chest compression rate, ventilations, compression fraction, pre-shock pause, post-shock pause, and/or perfusion index. Such a combination of information across multiple activities being performed on the patient may be used to generate a score or grade for the care provided to the patient, so as to indicate manners in which the rescuer can change subsequent care that is given. For example, measurements from the one or more CPR sensors may indicate that the rescuer is too excited or too relaxed in administering the CPR treatment (e.g., because the rescuer is applying compressions that are too deep or too shallow, or the rescuer is acting too quickly or too slowly in certain portions of the CPR interval). In such a situation, an indication may be provided for the rescuer to be more or less active in their care. Exemplary techniques for providing CPR performance information, including CPR quality feedback, are described in U.S. Pat. No. 8,738,129, filed on Nov. 14, 2011, and titled "Real-Time Evaluation of CPR Performance," and U.S. Pat. Pub. No. 2013/0296719, filed on Mar. 13, 2013, and titled "Rescue Performance Metric," the entire contents of both of which are hereby incorporated by reference.

Figure 6:
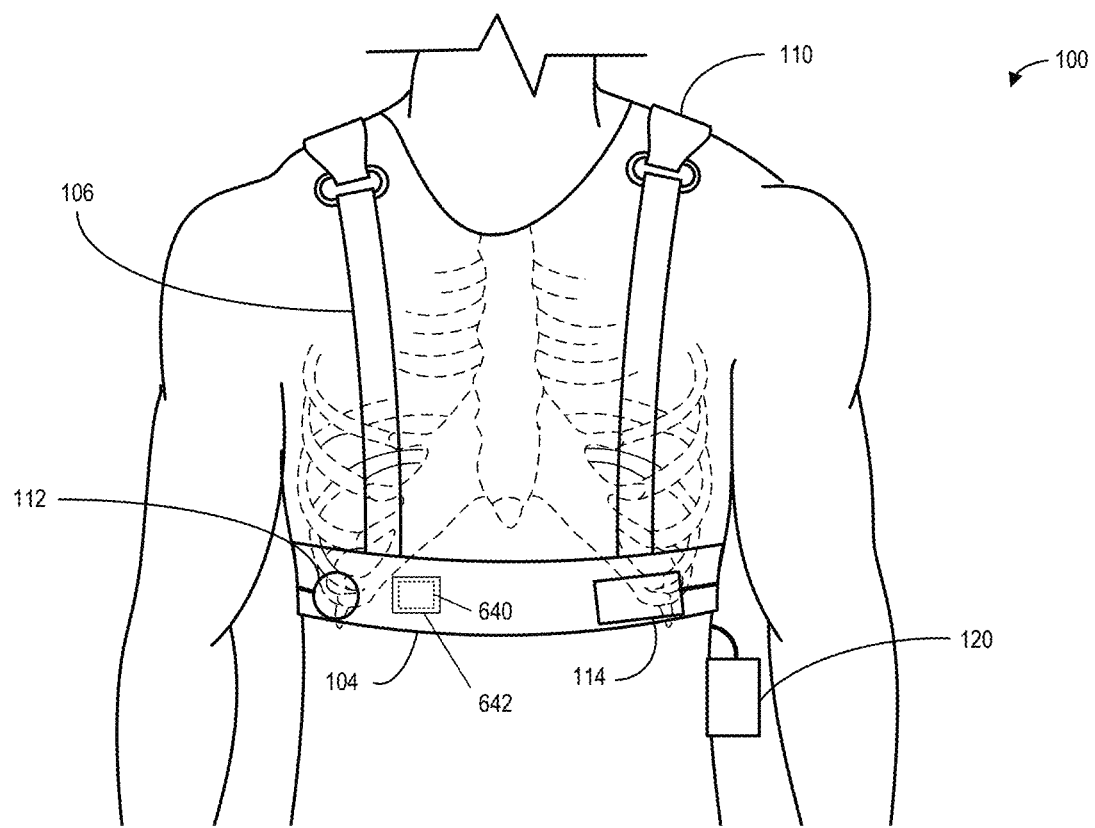
FIG. 6 shows an example of the wearable medical device that includes a wireless sensor stored in a waistband of the garment.

While the wearable medical device 100 shown in FIGS. 1A-1B has been described as storing the CPR sensor 140 in a flap 142 of the garment 110, in some implementations, the wearable medical device 100 includes one or more sensors that are stored elsewhere on the garment 110 (e.g., instead of or in addition to the CPR sensor 140 of FIG. 1). FIG. 6 shows an example of the wearable medical device 100 in which a wireless sensor 640 (e.g., sometimes referred to as a CPR sensor, a chest compression sensor, and/or a ventilation sensor) is stored in the waistband 104 of the garment 110. The wireless CPR sensor 640 may be configured to operate substantially similarly to the CPR sensor 140 described above with respect to FIGS. 1A-1B and 2A-2B.

The garment 110 can include a compartment that is configured to removably store the wireless CPR sensor 640. For example, the compartment may be a pocket 642 that is sewn into the garment 110 and configured to store the wireless CPR sensor 640 when CPR is not being administered. In this way, the patient does not experience the potentially cumbersome and/or uncomfortable placement of the wireless CPR sensor 640 when it is not needed.

Prior to administration of CPR, the wireless CPR sensor 640 may be removed from the pocket 642 and placed at the center of the patient's chest (e.g., above the xiphoid process). In some implementation, the pocket 642 may include a mechanism for closing the pocket 642, such as a zipper or a hook-and-loop fastener that prevents the wireless CPR sensor 640 from falling out of the pocket 642 when not in use. In some implementations, the pocket 642 may be positioned at another location of the garment 110 or at some other portion of the wearable medical device 100. For example, the wireless CPR sensor 640 may be stored in or on the controller 120 or the distribution node 130 when the wireless CPR sensor 640 is not needed.

While the CPR sensor 640 has been described as being a wireless sensor, in some implementations, the CPR sensor 640 may be connected to the controller 120 by one or more wires (e.g., via the distribution node 130).

As described above, it may be beneficial to position the chest compression sensor at the center of the patient's chest (e.g., above the patient's xiphoid process) to improve the accuracy of the compression depths as determined by the processor 318 of the controller 120. However, in some implementations, the wearable medical device 100 may be configured to primarily provide CPR feedback related to the rate of the chest compressions being administered; in such implementations, providing information related to the depths of the chest compressions may be a secondary concern, and thus the positioning of the chest compression sensor may be less critical.

Figure 7:
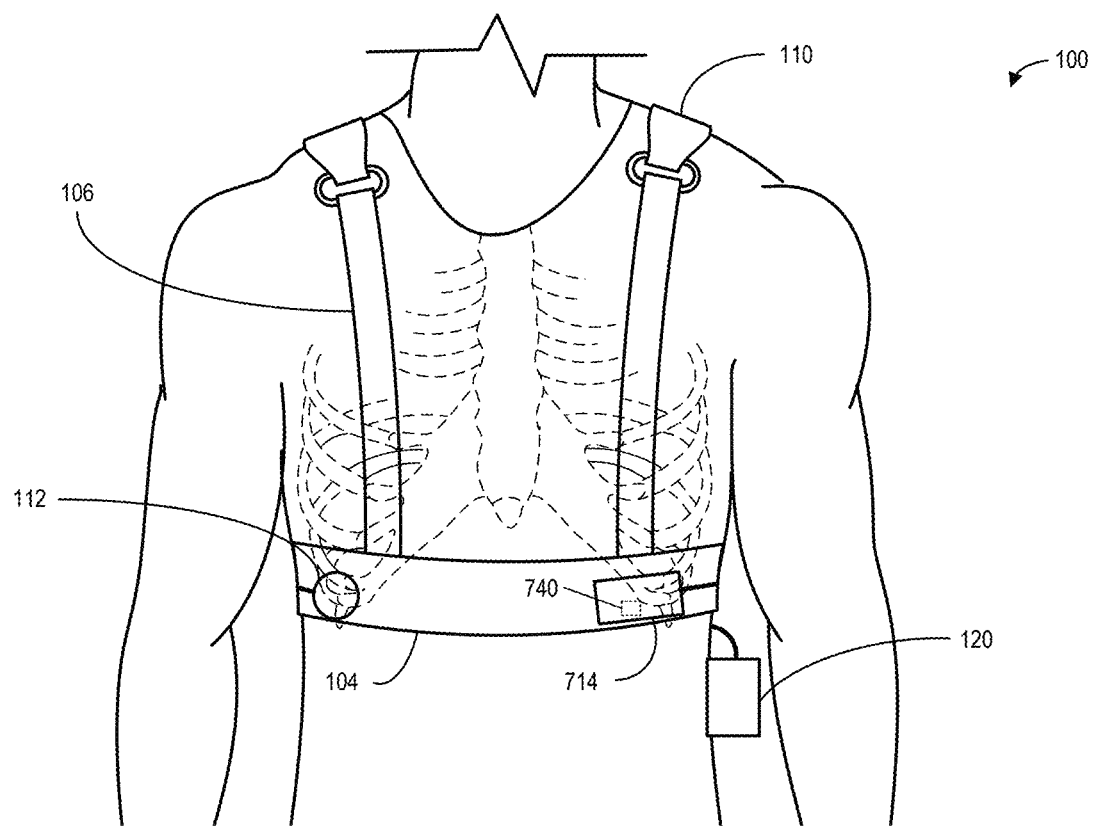
FIG. 7 shows an example of the wearable medical device that includes a sensor incorporated into a therapy electrode.

FIG. 7 shows an example of the wearable medical device 100 in which a sensor 740 (e.g., a CPR sensor, a chest compression sensor, and/or a ventilation sensor) is incorporated into one of the therapy electrodes 714. For example, the chest compression sensor 740 may be incorporated into the therapy electrode 714 that is positioned at the front/side of the patient's abdomen when the garment 110 is worn by the patient. The chest compression sensor 740 may be configured to operate substantially similarly to the chest compression sensors (140 of FIGS. 1A-1B and 2A-2B; 640 of FIG. 6) described above.

The therapy electrode 740 may include a sensor (e.g., a motion sensor) that is configured for measuring heart sounds of the patient. The sensor may include one or more accelerometers that detect motion information that is used for measuring the heart sounds. In some implementations, the sensor utilizes AUDICOR® Technology from Inovise Medical of Beaverton, Oreg. Typical accelerometer sensitivities appropriate for the measurement of chest compressions may be approximately +/−2 g full scale range, with data rates of approximately 100-2,000 Hz. Such a sensor may function as the CPR sensor 740 of FIG. 7.

In some implementations, the sensor utilizing AUDICOR® technology may be used to sense lung sounds in order to determine whether or not ventilations are being delivered by the rescuer in order to provide feedback to the rescuer on both the rate and timing of the delivered ventilations. In this case, when measuring the performance of ventilations (e.g., rather than chest compressions) during the course CPR, the sensor may be more adequately termed a "ventilation sensor" because it is not measuring chest compressions, but rather ventilator/pulmonary therapy.

The AUDICOR® sound sensor may act as a chest compression sensor by detecting heart sounds rather than chest wall motion due to compression of the chest, for example, by verifying adequacy of chest compressions via detection of heart valve closures that are the result of chest compressions.

As compressions are administered to the patient, the one or more accelerometers of the chest compression sensor 740 experience a rhythmic motion. A component of the motion signal detected by the accelerometer (e.g., the z-component of the acceleration signal) may include a series of peaks and valleys that correspond to the compressions. The motion signal is provided to the processor 318, and the processor 318 identifies compressions within the signal using a peak detection method. For example, each time the z-component of the acceleration signal crosses a predetermined threshold (e.g., a zero-crossing), the processor 318 may identify the occurrence of a compression. In some implementations, one or more integration, linear detrending, and/or voltage offset canceling steps may be performed on the data. Once the compressions are identified, the processor 318 correlates the compressions with the timings thereof to determine the rate of the chest compressions. The processor 318 may then instruction the wearable medical device to provide chest compression rate feedback information to the rescuer using the techniques described above with respect to FIGS. 4 and 5.

In some implementations, the motion data that the chest compression sensor 740 provides to the processor 318 may also be used to determine information related to the depths of the chest compressions, and such information may be used by the processor 318 to provide feedback related to compression depths. However, for the reasons described above, implementations in which compression depth feedback is desired may employ a chest compression sensor that can be repositioned to the center of the patient's chest (e.g., 140 of FIGS. 1A-1B or 640 of FIG. 6) or multiple chest compression sensors that are positioned at locations at the anterior of the patient's chest chosen to identify a characteristic of the center of the patient's chest, as described in more detail below.

While the chest compression sensor 740 has been described as being incorporated into the therapy electrode 714 that is positioned at the front/side of the patient's abdomen, the chest compression sensor 740 may be incorporated into any of the therapy electrodes 114 and/or positioned elsewhere on the wearable medical device 100. In some implementations, the chest compression sensor 740 may be positioned at the controller 120 or the distribution node 130. In some implementations, the chest compression sensor 740 may be positioned at one of the sensing electrodes or at any location on the garment 110.

Even when a chest compression sensor is not positioned at the center of the patient's chest, accurate compression depth information can be obtained by receiving motion data from multiple chest compression sensors positioned at various locations at the chest of the subject. The motion data from the multiple chest compression sensors can be mathematically adjusted to identify a characteristic of the center of the patient's chest. For example, the motion data from the multiple chest compression sensors can be used to infer the displacement of the center of the patient's chest during compressions.

Figure 8:
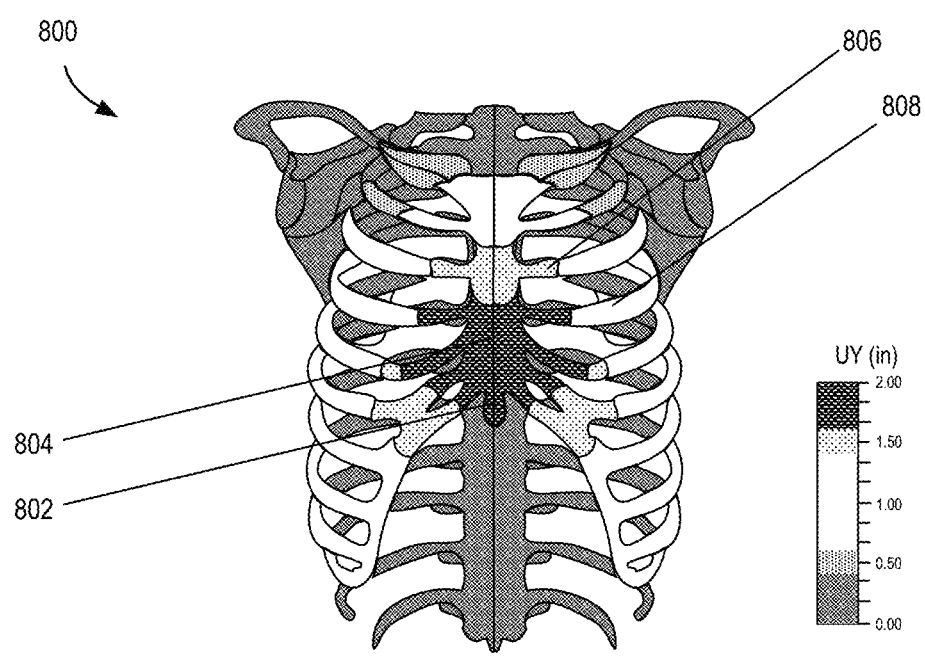
FIG. 8 shows an example representation of a chest of a patient.

FIG. 8 shows an example representation of a patient's chest 800. Chest compressions are applied by the rescuer placing his or her hands at the center of the patient's chest (e.g., above the xiphoid process 802) and applying downwards pressure in a rhythmic fashion. The sternum 804 connects to the patient's sternal cartilage 806, which connects to the ribs 808, and the entire chest reacts to chest compressions generally as a single unit.

While the chest structure reacts in a generally unified manner to the chest compressions, there can exist some degree of flex between the various portions of the patient's chest. For example, the patient's sternum 804 may flex relative to the sternal cartilage 806 and to a greater extent relative to the ribs 808. In this way, the sternum 804 may be displaced by a greater amount relative to the displacement of the sternal cartilage 806, and the sternal cartilage 806 may be displaced by a greater amount relative to the displacement of the ribs 808. The representation of the chest 800 includes shading that indicates such flexibility, where the portions of the chest that have a darker shades indicate a greater degree of displacement relative to portions of the chest that have lighter shades. For example, the representation 800 indicates the sternum 804 moves to a greater degree as compared to the other portions of the chest in response to chest compressions. In particular, the shading indicates that some portions of the sternal cartilage 806 experience a displacement of approximately 88.5% of the displacement of the sternum 804, and some portions of the ribs 808 experience a displacement of approximately 63.5% of the displacement of the sternum 804. Other portions of the patient's body (e.g., the clavicle, the spine, etc.) experience minimal and/or negligible displacement relative to the displacement of the sternum 804.

In knowing the relationships between the typical relative motions of the various portions of the patient's chest, it is possible to infer the displacement of the center of the patient's chest (e.g., the location above the xiphoid process) by measuring the displacement of one or more other locations of the chest. For example, suppose it was known that the tenth rib (e.g., the bottom rib) is always displaced at 50% of the displacement of the center of the patient's chest. One could position a motion sensor (e.g., a CPR sensor) at the tenth rib, measure the displacement, multiply the displacement by a correction factor of two, and determine the displacement at the center of the chest. In practice, however, such a conversion may not be so simple because the human body is not uniform from patient to patient.

Various different patient characteristics may impact the relative flexibilities of the different portions of the chest. For example, a person having a wide chest may exhibit a greater disparity between the displacement of the sternum 804 and the displacement of the ribs 808, or older patients may exhibit less displacement disparity (e.g., due to calcification in body tissue). Also, due to different chest dimensions across different patients, the motion sensor may not be positioned on the patient exactly where expected, thereby introducing error into the displacement conversion. Further, while the magnitude of displacement may be known for the various portions of the patient's chest, additional motion information may be helpful to determine the characteristics of the chest compressions. For example, rotational displacement measurements (e.g., tilt measurements) of the chest relative to the floor, which typically results from chest compression, may provide useful information that can be considered in determining the depths of the compressions. In some implementations, such information may be more accurately obtained by including multiple chest compression sensors on the wearable medical device 100 and/or by fitting and calibrating the wearable medical device 100.

In some implementations, before the wearable medical device 100 is first used by the patient, one or more parameters related to the patient's chest measurements may be provided. Such parameters may be provided via the user interface 318 of the controller 120 (e.g., via the touch screen 220 of FIGS. 2A-2B). Examples of measurements that may be provided include the transverse diameter (e.g., width) of the chest, the anterior-posterior diameter (e.g., length between the sternum and the spine) of the chest, and the distance between the waistband 104 of the garment 110 and the patient's xiphoid process, among others.

Using the provided patient measurements and/or other patient parameters, the wearable medical device 100 may be configured to adjust an algorithm for determining the displacement of the center of the patient's chest to better fit the particular patient. For example, in an uncalibrated state, the wearable medical device 100 may use a default chest motion model for determining the displacement of the center of the patient's chest relative to the displacement of one or more other locations of the chest. Referring again to FIG. 8, the default chest motion model may cause the wearable medical device 100 to multiply displacement measurements by a correction factor that corresponds to the relative shading of the chest representation 800. In other words, the chest representation 800 shown in FIG. 8 may represent a default chest motion model that indicates particular correction factors that are to be applied to motion measurements from one or more motion sensors.

Should the patient's particular chest measurements deviate from those of the default chest motion model, the model may be refined accordingly. For example, if the dimensions of the patient's chest are smaller than the values assumed for the default model, the correction factors may need to be adjusted accordingly (e.g., reduced); if the dimensions of the patient's chest are larger than the values assumed for the default model, the correction factors may need to be adjusted accordingly (e.g., increased). The appropriate adjustments may be based on experimental data measurements obtained from a number of patients having various chest dimensions. In this way, the wearable medical device 100 may be calibrated to provide CPR feedback information that tends to be more accurate for patients who have characteristics in line with the particular patient.

Continuing with the example provided above, suppose the default chest motion model is based on relative chest motions of a patient having chest dimensions typically seen in an adult male. That is, based on experimental data, the default chest motion model may indicate that displacements measured at the tenth rib (e.g., the bottom rib) should be multiplied by a correction factor of two in order to infer the motion at the center of the patient's chest (e.g., because the tenth rib is only displaced at 50% of the displacement of the center of the patient's chest). However, experimental data may also indicate that in patients having smaller chest dimensions, the tenth rib typically experiences a displacement relative to the center of the patient's chest that is significantly smaller (e.g., 40%). Thus, to more accurately infer the motion of the center of such a patient's chest based on displacement measurements taken at the tenth rib, it may be more appropriate to multiply the displacement measurements by a correction factor of 2.5. The values provided here are exemplary and are being used simply to illustrate the idea that the wearable medical device 100 may consider various patient characteristics, including chest dimensions, in determining information about the CPR therapy being administered.

Figure 9:
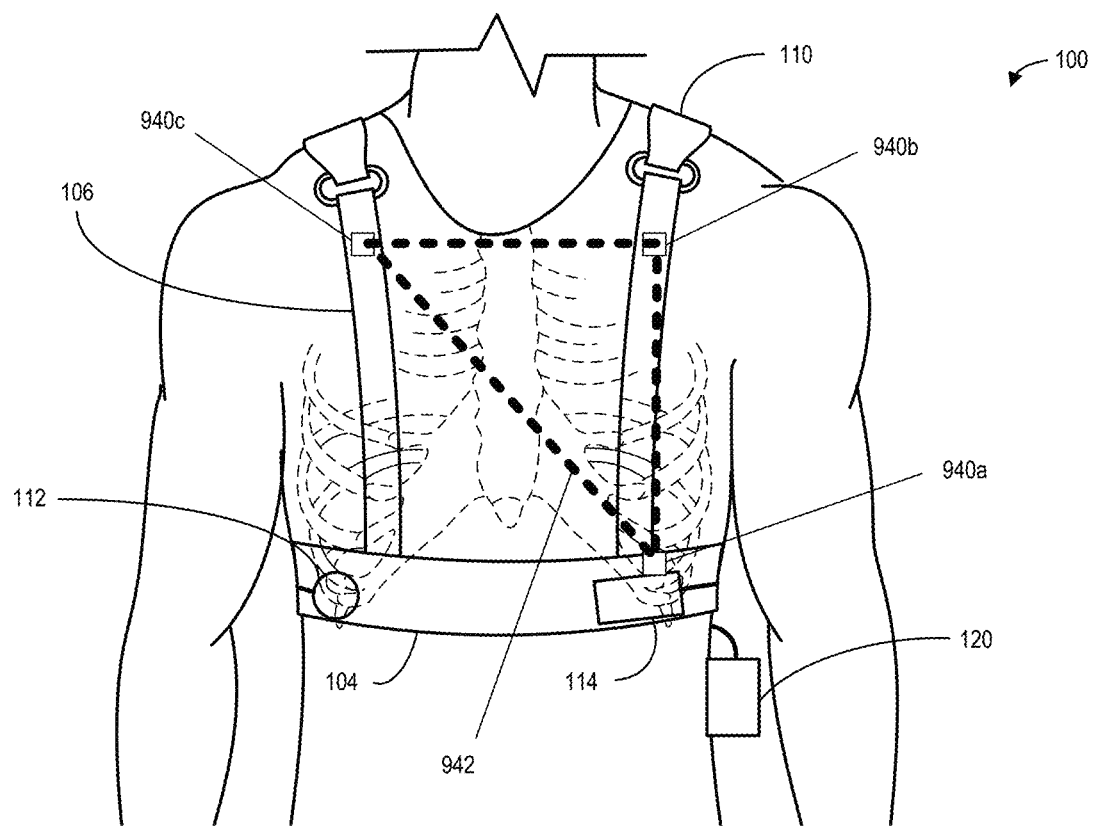
FIG. 9 shows an example of the wearable medical device that includes three sensors for detecting characteristics of a CPR therapy.

As mentioned above, in addition to calibrating the wearable medical device 100 for a particular patient or a particular type of patient, the motion of the center of the patient's chest may be inferred more accurately when motion data from multiple sensors situated at different locations on the chest are obtained. FIG. 9 shows an example of the wearable medical device 100 that includes three sensors 940*a-c* (e.g., sometimes referred to as CPR sensors, chest compression sensors, and/or ventilation sensors) for detecting characteristics of the CPR therapy. The chest compression sensors 940*a-c* may include one or more accelerometers that are configured to detect motion that occurs during the administration of CPR. In this example, a first chest compression sensor 940*a* is positioned at the side of the waistband 140 of the garment 110, a second chest compression sensor 940*b* is positioned on one of the shoulder straps 106 of the garment 110, and a third chest compression sensor 940*c* is positioned on the other shoulder strap 106 of the garment 110. The chest compression sensors 940*a-c* define a triangular plane 942 on the chest of the patient. The medical device controller 120 is configured to process information (e.g., motion information) received from the chest compression sensors 940*a-c* and provide information about the CPR therapy. For example, the controller 120 is configured to determine information related to the motion of the triangular plane 942 as chest compressions are being administered.

The chest compression sensors 940*a-c* are configured to detect characteristics of the chest compressions, such as the depth and rate of chest compressions administered to the patient. For example, accelerometers incorporated into the chest compression sensors 940*a-c* may provide acceleration, velocity, and/or displacement information to the controller 120, and the controller 120 can process the information to determine the depths of the chest compressions and the rate at which the chest compressions are administered.

As mentioned above, the depths of chest compressions are typically measured at the center of the patient's chest (e.g., at a location above the patient's xiphoid process). In this way, the depth of a chest compression may be a measure of the displacement of the center of the patient's chest from an initial position (e.g., with no pressure applied to the chest) to a compressed position (e.g., when peak pressure is applied to the chest). Because none of the chest compression sensors 940*a-c* are positioned at the center of the patient's chest, the depths of chest compressions can be determined by performing additional processing (e.g., mathematical adjustments) of the motion information received from the chest compression sensors 940*a-c*.

In some implementations, one or more correction factors may be applied to the motion information to infer the displacement of the center of the patient's chest during compressions. For example, the displacement information received from the second and third chest compression sensors 940*b*, 940*c* may be multiplied by a first correction factor, and the displacement information received from the first chest compression sensor 940*a* may be multiplied by a second correction factor. The corrected displacement information from the three chest compression sensors 940*a-c* may then be averaged in order to infer the displacement that occurs at the center of the patient's chest (e.g., the depth of the chest compressions).

The chest compression sensors 940*a-c* define a triangular plane 942 on the chest of the patient. In some implementations, the motion information from the chest compression sensors 940*a-c* is used to determine the motion of the triangular plane 942. For example, if the displacement over time of the three vertices of the triangular plane 942 is known, the displacement of any position of the triangular plane 942 (e.g., including the portion of the triangular plane 942 that resides at the center of the patient's chest) can be determined using appropriate mathematical adjustment. The inclusion of additional chest compression sensors may further improve the accuracy of such determinations.

In some implementations, one or more of the chest compression sensors 940*a-c* is configured to measure information related to tilt (e.g., relative to a reference plane). The tilt information can be used to determine the rotational displacement of the chest. For example, when compressions are applied to the patient's chest, the chest experiences a rotational displacement about an axis near the top of the patient's chest. chest compression sensors positioned toward the bottom of the chest (e.g., the first chest compression sensor 940*a*) will experience relatively more displacement due to the rotation than chest compression sensors positioned toward the top of the chest (e.g., the second and third chest compression sensors 940*b*, 940*c*). In some implementations, it may be desired to differentiate between displacement due to the rotation and substantially vertical displacement. For example, the substantially vertical displacement may be the appropriate measure to use for determining the actual depths of the chest compressions.

Tilt information determined by individual ones of the chest compression sensors 940*a-c* can be provided to the processor 318, and the processor 318 can consider the tilt information to properly account for the rotational displacement. In some implementations, the tilt information is used to adjust the correction factor to be applied to motion information from a particular one of the chest compression sensors 940*a-c*. In some implementations, instead of or in addition to individual ones of the chest compression sensors 940*a-c* being configured to provide tilt information, motion data from two or more of the chest compression sensors that reside at different vertical locations of the patient's chest may be used to infer the tilt of the patient's chest relative to the floor. For example, the displacement measured by the first chest compression sensor 940*a* and the second chest compression sensor 940*b*, or the displacement measured by the first chest compression sensor 940*a* and the third chest compression sensor 940*c*, may be used to determine the angle of the patient's chest relative to the floor that results from the application of chest compressions.

In some versions of the wearable medical device 100, there may not be a convenient location to place the CPR sensor. For example, conventional state-of-the-art chest measurement sensors require that the motion sensor be placed directly on the patient's sternum (e.g., at the location where the rescuer delivers the chest compressions). With conventional methods of measuring chest compression characteristics, if the chest compression sensor is offset by any amount from underneath where the rescuer is delivering the compressions, then the accuracy measurement can be significantly degraded. It can be uncomfortable for the patient to have a portion of the garment continuously covering the sternal portion during daily use. It may therefore be preferable for the chest compression sensor to be placed in an already-existing portion of the garment. Such portions of the garment are parasternal (i.e. located off of the patient's sternum).

In order to allow for the chest compression sensor to be placed parasternally and still achieve satisfactory accuracy in the measurement of chest compressions, a representation of the geometry of the patient's chest may be used by the wearable medical device 100 to determine particular adjustments to the motion data that can be applied to determine chest compression characteristics with enhanced accuracy. In the simplest embodiment, the geometric representation of the patient's chest used to determine particular adjustments to the motion data may be a preprogrammed, generic representation based on known statistical anthropometric data collected from a relevant patient population. The adjustments may be in the form of a table lookup, a linear adjustment function, or a non-linear adjustment function. There may be separate adjustments (e.g., tables) for different patient populations, for instance, separate tables for women, men, and potentially different weight groups.

Figure 10:
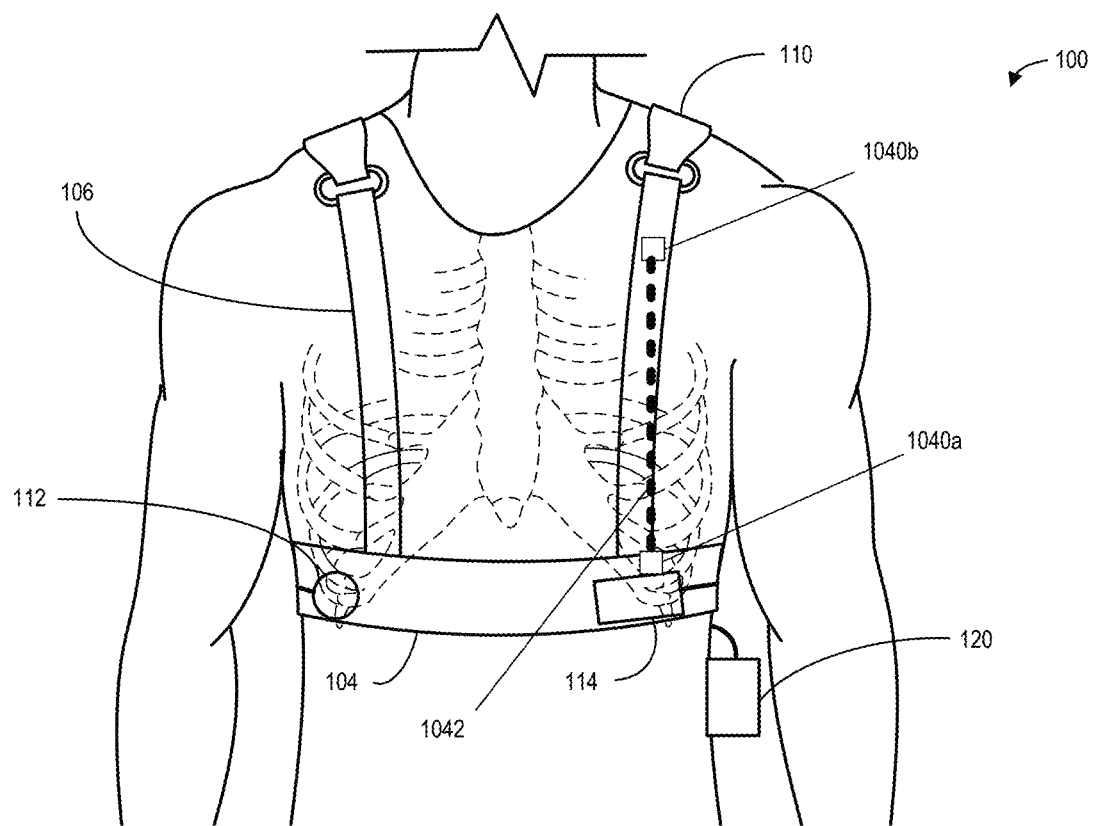
FIG. 10 shows an example of the wearable medical device that includes two sensors for detecting characteristics of a CPR therapy.

The motion of the center of the patient's chest may also be estimated using two sensors positioned at different parasternal locations on the chest. FIG. 10 shows an example of the wearable medical device 100 that includes two chest compression sensors 1040a, 1040b for detecting characteristics of the CPR therapy. The chest compression sensors 1040a, 1040b may include one or more accelerometers that are configured to detect motion that occurs during the administration of CPR. In this example, a first chest compression sensor 1040a is positioned at the side of the waistband 104 of the garment 110 and a second chest compression sensor 1040b is positioned at one of the shoulder straps 106 of the garment 110. In some implementations, the second chest compression sensor 1040b is positioned at the other shoulder strap 106 of the garment 110 (e.g., the shoulder strap 104 diagonal from the first chest compression sensor 1040a). The chest compression sensors 1040a, 1040b define a line 1042 on the chest of the patient. The controller 120 is configured to process information (e.g., motion information) received from the chest compression sensors 1040a, 1040b and provide information about the chest compressions. For example, the controller 120 is configured to determine information related to the motion of the line 1042 as CPR is being administered.

The chest compression sensors 1040a, 1040b are configured to detect characteristics of the CPR in a manner substantially similar to that described above with reference to the sensors 940a-c of FIG. 9. For example, accelerometers incorporated into the chest compression sensors 1040a, 1040b may provide acceleration, velocity, and/or displacement information to the controller 120, and the controller 120 can process the information to determine the depths of the chest compressions and the rate at which the chest compressions are administered. The information received from the chest compression sensors 1040a, 1040b may be mathematically adjusted (e.g., by a correction factor) to infer the depths of chest compressions at the center of the patient's chest. In some implementations, the angle of the chest relative to the floor may be determined based on a comparison of the displacement information of the chest compression sensors 1040a, 1040b and/or information related to tilt as measured by the individual ones of the chest compression sensors 1040a, 1040b.

The description related to FIGS. 8-10 explains that the accuracy of the measurements of the chest compression therapy that are determined can be improved by providing patient characteristic information (e.g., chest measurements) and/or by including additional chest compression sensors; knowing the patient's chest measurements can help to refine the appropriate correction factor to be applied to the motion data, and inclusion of additional sensors can minimize variation between an expected location of a chest compression sensor and the actual location of the sensor on the patient. However, the accuracy of the chest compression characteristics may be even further improved by providing more extensive patient thoracic geometry information so as to tailor the wearable medical device 100 to a particular patient. For example, chest measurement information that provides a representation of the geometry of the particular patient's chest may be used by the wearable medical device 100 to determine particular adjustments to the motion data that can be applied to determine chest compression characteristics of enhanced accuracy. Alternatively, simple estimates of patient geometry—e.g., size-related: "small", "medium", or "large"; or chest conformation-related: "barrel-chested", "flat-chested", "narrow", "wide", etc.—may be utilized to enhance the accuracy.

In some implementations, information related to the geometry of the particular patient's chest may be determined prior to initiation of CPR. In this way, the correction factors to be applied to the motion data from the chest compression sensors may be tailored to the particular patient, thereby resulting in more accurate compression depth and/or rate detection, and in turn more accurate feedback provided to the rescuer.

Figure 11:
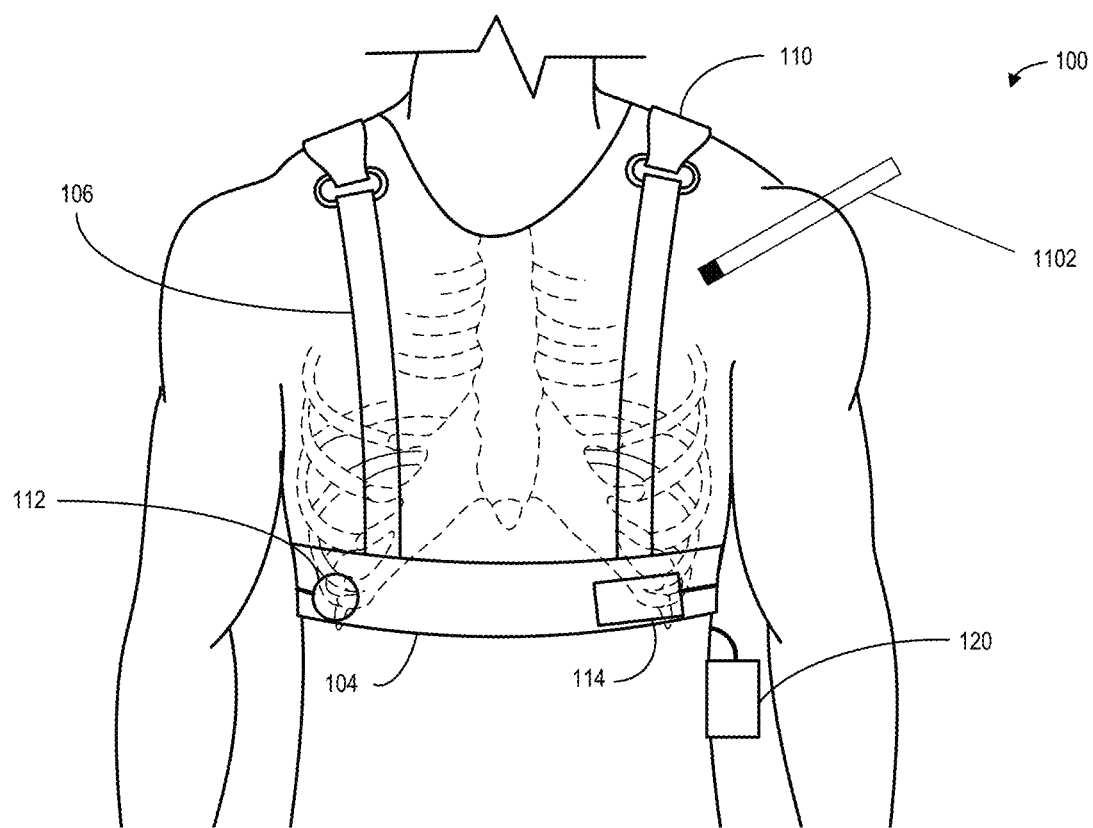
FIG. 11 shows an example of a device that can be used to measure information related to a geometry of a patient's chest.

FIG. 11 shows an example of a measuring device, such as a wand 1102, that can be used to measure information related to a geometry of the patient's chest prior to initiation of CPR. The wand 1102 may include one or more motion sensors that are configured to provide information to the controller 120 that identifies the coordinates of the wand 1102. The motion sensors may include one or more accelerometers that are configured to measure acceleration, velocity, displacement, and/or tilt information and provide such information to the controller 120. In some implementations, the motion sensors are configured to measure motion and/or positional information in three axes. The one or more motion sensors may be positioned at a tip of the wand 1102 and/or throughout the wand 1102.

The geometry of the particular patient's chest may be determined by moving the wand 1102 around the various portions of the patient's chest. For example, the wand 1102 may be placed at an initial position (e.g., a known position), the three dimensional coordinates of which are known to the controller 120. As the wand 1102 navigates the contours of the patient's chest, motion and/or positional information (e.g., related to acceleration, velocity, displacement, and/or tilt) is provided to the controller 120. Such information can be used to continuously (e.g., substantially continuously) determine the position of the wand 1102 relative to the starting position, thereby providing a mapping of the geometry of the patient's chest commensurate with the amount of positional locations gathered by the wand 1102.

The completeness of the determined geometry of the chest may be proportional to the number of positional locations gathered by the wand 1102. In some implementations, it may be sufficient to map a discrete number of chest locations of the patient. For example, the wand 1102 may be used to map coordinates to particular chest locations of interest, such as the patient's xiphoid process, sternal notch, inferior margin of the ribs (e.g., bottom of the ribs), individual ribs, and/or the perimeter of the ribcage, among others. The mapping information can be used to generate a representation of the patient's chest.

In some implementations, the wand 1102 is also used to map the coordinates of the one or more chest compression sensors relative to locations on the patient's chest. For example, when the wand 1102 is positioned at a location of a chest compression sensor, an indication may be provided to the controller 120 (e.g., via the touch screen 220) indicating such. In some implementations, the wand 1102 and the chest compression sensors are configured to communicate with each other through a wireless and/or a wired connection. For example, the wand 1102 and the one or more chest compression sensors may include electrical contacts. When the wand 1102 is positioned at a location where a chest compression sensor resides, the electrical contacts may touch each other. The contact between the wand 1102 and the chest compression sensor may indicate to the controller 120 that the coordinates of the wand 1102 are to be mapped to the position of the particular chest compression sensor. Using this technique, the controller 120 may obtain a complete representation of the particular patient's chest that can be used to determine the dimensions and contours of the chest, including the anterior-posterior diameter and transverse diameter of the chest, among others. The representation can include the coordinates of the various portions of the chest and the coordinates of the one or more chest compression sensors relative to the various portions of the chest. Using the information included in the representation, the controller 120 can infer how the center of the patient's chest responds relative to the motion of the chest locations where the one or more chest compression sensors are positioned. In this way, the controller 120 can process the motion information obtained from the one or more chest compression sensors in conjunction with the information contained in the chest representation to determine the motion that occurs at the at the center of the patient's chest.

In some implementations, a 3D representation (e.g., a 3D model) of the patient's chest may be generated based on the information obtained from the wand 1102. For example, a representation similar to that shown in FIG. 8 may be generated based on the coordinate mapping. In some implementations, the 3D representation may include similar shading that indicates the expected relative motions of the various portions of the patient's chest in response to chest compressions. Such information may be used to determine an appropriate correction factor to be applied to motion information obtained from particular chest compression sensors to infer the displacement of the center of the patient's chest during compressions.

In some implementations, the information related to the geometry of the patient's chest and/or the representation of the patient's chest may be used to determine optimal placement of the chest compression sensors. In some examples, the garment 110 may provide multiple possible locations for positioning the one or more chest compression sensors. For example, multiple hook-and-loop fasteners and/or multiple compartments may be positioned at various locations on the garment 110. Based on the determined geometry information and/or representation of the patient's chest, the wearable medical device 100 may suggest that the chest compression sensors be placed at particular locations. For example, briefly referring to FIG. 9, suppose the patient has a unique chest geometry that results in the first chest compression sensor 940a being positioned too far to the middle of the patient's chest (e.g., such that the first chest compression sensor 940a does not reside over the patient's ribs). As explained above, because the entire chest generally moves as a single unit during administration of chest compressions, a chest compression sensor that is not positioned over the patient's ribs may provide motion information that is of limited value. In some implementations, the waistband 104 of the garment 110 may include multiple compartments positioned along the upper portion of the waistband 104. Based on the determined geometry of the patient's chest and the determined relative positions of the chest compression sensors 940a-c, the wearable medical device 100 may suggest that the patient move the first chest compression sensor 940a to a different compartment of the garment 110. For example, the wearable medical device 100 may instruct the patient to move the first chest compression sensor 940a to a lateral compartment that resides over the patient's lower ribs. In some implementations, the wearable medical device 100 may also or instead suggest that the patient swap the garment 110 for another garment having a size that is more appropriate for the patient's chest geometry.

After characteristics of the CPR therapy (e.g., including the rate and/or depths of chest compressions) are determined with the help of the information related to the geometry of the patient's chest, the controller 120 is configured to provide information related to the CPR therapy to the output device (324 of FIG. 3). The information that can be provided is substantially similar to that which is described above with respect to FIGS. 4 and 5. For example, the controller 120 may provide visual and/or audio information related to compression depths and/or compression rate via the touch screen 220 and/or the speaker 204. The information may be provided in the form of feedback for assisting the rescuer in refining the CPR therapy. For example, the feedback may include rhythmic audio tones indicative of a target rate of chest compressions and/or verbal commands that instruct the rescuer to speed up the compression rate, slow down the compression rate, increase the depths of compressions, and/or decrease the depths of compressions, among others.

Alternative Implementations

While certain implementations have been described, other implementations are possible.

While the device for measuring information related to the geometry of the patient's chest has largely been described as a wand that includes motion sensors (e.g., the wand 1102 of FIG. 11), other implementations are possible. For example, in some implementations, the measuring device may include one or more cameras that are configured to scan a surface of the patient's chest. The scan may include capturing multiple images of the patient's chest from multiple angles and/or by the multiple cameras. The processor of the medical device controller is configured to generate a 3D representation of the patient's chest using the information obtained by the scan, and the representation can be used to determine dimensions and contours of the chest. In this way, a 3D model of the patient's chest may be generated. The 3D model may be in the form of a 3D polygon surface mesh. In some implementations, a 3D surface imaging technology with anatomical integrity can be used, such as the 3dMDthorax System available from 3dMD LLC of Atlanta, Ga.

In some implementations, the one or more cameras may be used to map coordinates to particular chest locations of interest, such as the patient's xiphoid process, sternal notch, inferior margin of the ribs, individual ribs, and/or the perimeter of the ribcage, among others. In some implementations, the one or more cameras may be used to measure information related to the geometry of the patient's chest while the patient is wearing the medical device. In this way, the one or more cameras may be used to map the coordinates of the one or more chest compression sensors relative to locations on the patient's chest.

Each of the one or more chest compression sensors may include a visual identifiers (ID) that may indicate the particular chest compression sensor and information related to the particular chest compression sensor. For example, briefly referring to FIG. 9, each of the chest compression sensors 940a-c may include a visual ID that indicates the general position of the corresponding chest compression sensor 940a-c; the visual ID of the first chest compression sensor 940a may indicate that it is positioned on the waistband 104 of the garment 110, the visual ID of the second chest compression sensor 940b may indicate that it is positioned on the left shoulder strap 106 of the garment 110, and the visual ID of the third chest compression sensor 940c may indicate that it is positioned on the right shoulder strap 106 of the garment 110. The visual IDs may be in the form of a barcode or a QR code, to name a few. The one or more cameras are configured to identify the visual ID by comparing the captured image information to stored data (e.g., data stored in a database).

The one or more cameras along with the processor of the medical device controller may be configured to determine the actual location of the chest compression sensors 940a-c relative to their expected locations. For example, with respect to the second chest compression sensor 940b, the wearable medical device 100 may expect the second chest compression sensor 940b to be positioned at the middle of the patient's third rib (e.g., the third rib from the top). That is, the wearable medical device 100 may be calibrated such that motion information received from the second chest compression sensor 940b is mathematically modified based on an assumption that the second chest compression sensor 940b is positioned at the middle of the patient's third rib. Referring also to the representation 800 of FIG. 8, if the second chest compression sensor 940b is actually positioned elsewhere (e.g., at the sternal cartilage 806 adjacent to the patient's third rib), the second chest compression sensor 940b may experience more displacement as a result of chest compressions than expected. Thus, it may be appropriate to modify the correction factor applied to the second chest compression sensor's 940b motion information to account for the positional disparity.

In some implementations, the controller may suggest that an alternative garment be used by the patient such that the chest compression sensors are positioned more closely to their expected positions. In some examples, the garment may be available in multiple sizes that each position the chest compression sensors slightly differently relative to each other. If the image information indicates that the chest compression sensors are generally positioned too centric on the patient's chest, the controller may suggest that the patient switch to a larger sized garment. The patient may then undergo a new scan to determine whether the larger garment serves to position the chest compression sensors more appropriately. In some implementations, slight deviations between the expected and actual positions of the chest compression sensors may be alleviated by mathematically adjusting the received motion information in the manner described above.

In some implementations, once the information related to the geometry of the patient's chest is obtained by the one or more cameras and/or the representation of the patient's chest is generated, the medical device controller may use such information in substantially the same ways as described above with respect to FIG. 11. For example, the information and/or the representation can be used to determine the dimensions and contours of the chest, including the anterior-posterior diameter and transverse diameter of the chest, among others. The representation can include the coordinates of the various portions of the chest and the coordinates of the one or more chest compression sensors relative to the various portions of the chest. Using the information included in the representation, the controller can infer how the center of the patient's chest responds relative to the motion of the chest locations where the one or more chest compression sensors are positioned. In this way, the controller can process the motion information obtained from the one or more chest compression sensors in conjunction with the information contained in the chest representation to determine the motion that occurs at the at the center of the patient's chest during CPR.

In some implementations, the wearable medical device may be configured to determine a location of a rescuer's hand during administration of the CPR treatment, including chest compressions. That is, the processor of the medical device controller may be configured to process information related to the location of the rescuer's hand and present information to the rescuer based on the determined location and/or positioning. In some implementations, the location of the rescuer's hand may be inferred based on information received from the one or more chest compression sensors.

In some implementations, the wearable medical device may include one or more components for determining the amount and/or location of pressure applied to the patient's chest during administration of chest compressions. For example, the garment may include a pressure sensitive fabric that is configured to convey to the processor information related to the location and/or magnitude of pressure being applied.

In some implementations, the pressure sensitive fabric resides at or near the center of the patient chest. The pressure sensitive fabric may be in the form of a strain sensor. For example, the pressure sensitive fabric may include one or more conductive elements (e.g., including inductive elements and/or capacitive elements) that are incorporated into the fabric of the garment. The conductive elements are configured to stretch, expand, and/or otherwise deform with the fabric of the garment. Thus, when pressure is applied to the fabric during the administration of chest compressions, the fabric and the conductive elements deform with the fabric.

The inductive element may include a conductive wire or thread that is configured in a coiled pattern (e.g., spring shaped) that includes a plurality of windings (or turns). In some implementations, a magnetic core may be disposed within the windings. In some implementations, the inductive element may be configured in a serpentine patter that includes a plurality of serpentine turns. The capacitive element may include conductive wires of threads configured in parallel with each other in a coiled or serpentine pattern. In some implementations, the capacitive element includes two wires with a space therebetween. The space can be occupied by an insulator, a dielectric material, or air such that the two wires act as a capacitor when supplied with power. The inductive element and/or the capacitive element can be shielded, jacketed, or insulated, and may be configured to connect to the controller to receive power.

When the pressure sensitive fabric and the conductive elements are deformed, the radii of the windings or turns of the coiled or serpentine pattern change. When these radii change, the inductance of the inductive element and/or the capacitance of the capacitive element changes. One or both of the inductive element and the capacitive element can provide a measured value (e.g., an inductance value or a capacitance value) to the controller that is indicative of a magnitude of deformation experienced by the pressure sensitive fabric. Further, the controller can determine precisely where pressure is being applied based on which of the capacitive elements and/or inductive elements are deformed and supplying signals to the controller.

While the processor of the medical device controller has been described as being configured to provide information about the CPR therapy to the output device that includes rate of chest compressions and depths of chest compressions, the processor may provide other information as well. In some implementations, the processor is configured to cause the output device to provide feedback to the rescuer related to the positioning of the rescuer's hands. For example, based on the readings received from the pressure sensitive fabric, the processor may determine that the rescuer is not applying chest compressions at the appropriate location. The processor may cause the output device (e.g., the touch screen and/or the speaker of the controller) to instruct the rescuer to adjust his or her hand positioning accordingly. For example, the speaker may provide a verbal command to "move your hands higher on the chest" or "move your hands lower on the chest," among others. In some implementations, the touch screen may provide a schematic of a patient chest that includes a target location where chest compressions should be applied and an actual location where the compressions are being applied; the touch screen may instruct the rescuer to move his or her hands to the target location indicated in the schematic.

In some implementations, the information received from the pressure sensitive fabric may be used to determine or assist in determining the depths of the compressions being applied to the patient. However, in some implementations, it may be more important to directly measure how deeply the rescuer is compressing the chest than to measure how hard the rescuer is pressing; thus, a pressure reading alone may be insufficient for providing complete feedback related to the depths of the chest compressions.

In some implementations, one or more chest compression sensor may be positioned behind the patient (e.g., on the back of the patient) when the garment is worn by the patient. Motion information received from the chest compression sensor positioned on the patient's back may be considered by the medical device controller to more accurately determine characteristics of the CPR therapy. In some implementations, CPR may be performed on a patient lying on a soft surface. When chest compressions are applied to the patient, the patient's entire body may move in response. That is, while a portion of the rescuer's compressions applied to the center of the patient's chest may result in desired compressions to the chest, some of the compression effort may result in movement of the patient's entire body. The movement of the entirety of the patient's body may result in motion artifacts that skew the motion data received from the chest compression sensors.

For example, a first chest compression sensor positioned on the front surface of the patient's chest (e.g., at the center of the patient's chest) may indicate a displacement of three inches in response to chest compressions applied to a patient who is lying on a soft bed. While the first chest compression sensor may be displaced by a total amount of three inches, the entirety of the patient's body may be displaced by two inches due to the softness of the bed. Thus, the net compressions of the front surface of the patient's chest relative to the patient's back is only one inch. Unless the wearable medical device is provided with some frame of reference, it may erroneously determine that compressions are being applied with a depth of three inches and instruct the rescuer to apply compressions having less depth.

In some implementations, a second chest compression sensor is positioned on the back of the patient (e.g., in a back portion of the garment 110) substantially behind the first CPR sensor. The second chest compression sensor experiences motion due to the entirety of the patient's body depressing into the soft bed, but may not experience motion that corresponds to the front surface of the patient's chest moving relative to the patient's back. In some implementations, the motion information received from the second chest compression sensor may be subtracted from the motion information received from the first chest compression sensor to offset the effects of the universal motion. Using the motion information from both sensors, the wearable medical device can correctly determine that the chest compressions are resulting in compressions depths of only one inch, and thereby instruct the rescuer to apply compressions having more depth.

In some implementations, the motion information received from the second chest compression sensor may be used to mathematically adjust the motion information from the first chest compression sensor in some other fashion. In some implementations, each chest compression sensor positioned on the front surface of the patient's chest has a corresponding chest compression sensor positioned on the patient's back substantially behind the chest compression sensor on the front surface.

In some implementations, as chest compressions are administered, the patient's sternal cartilage may soften, resulting in increased motion of the sternum relative to the other portions of the patient's chest. To account for the softening, the controller may be configured to adjust the correction factor commensurate with the length of time that the compressions have been administered. In some implementations, the correction factor applied to motion data received from one or more sensors may increase over time accordingly.

While the wearable medical device has been largely described as providing information (e.g., feedback information) related to the CPR therapy during administration of the CPR, in some implementations, such information is provided after or in between portions of CPR therapy. For example, feedback information may be provided to the rescuer after a series of chest compressions have been applied. In this way, the feedback does not overwhelm the rescuer during administration of a portion of treatment. In some implementations, the wearable medical device may determine that CPR therapy is no longer needed, and the feedback may include an instruction to cease administration of CPR. In some implementations, the wearable medical device may instruct the rescuer to temporarily cease administration of CPR. For example, the wearable medical device may determine that a therapeutic shock should be applied to the patient (e.g., by the therapy electrodes); the wearable medical device may instruct the rescuer to not touch the patient and/or step away from the patient prior to the shock being delivered.

In some implementations, the wearable medical device may instruct the patient to temporarily cease administration of CPR before performing an ECG analysis of the patient (e.g., to determine how the patient is responding to the therapy). In some implementations, if the analysis were to be performed during the chest compressions, the chest compressions may affect the sensed electrical rhythm. In some implementations, an ECG analysis can be performed during pauses between sets of compressions (for example, during a pause after every fifth chest compression). In one example, the wearable medical device may initially determine that the patient is experiencing a non-shockable rhythm such as bradycardia, in which case CPR should be administered in order to keep the patient alive; during a subsequent ECG analysis, the wearable medical device may determine that the patient's heart rhythm has changed to ventricular fibrillation, in which case CPR should be ceased to allow the wearable medical device to perform more analysis and possibly apply one or more shocks to the patient. The wearable medical device may instruct the rescuer accordingly. In this way, the rescuer is integrated into a scheme that allows complex combinations of therapy.

In some implementations, one or more of the CPR sensors may be incorporated into a OneStep™ electrode that is configured to provide defibrillation, pacing, and/or CPR assistance to the user. The OneStep™ electrode may include one or more accelerometers and/or gyroscopes for measuring motion data.

Example Infrastructure

Software running on the medical device controller can be realized by instructions that upon execution cause one or more processing devices to carry out the processes and functions described above. The instructions can include, for example, interpreted instructions such as script instructions, or executable code, or other instructions stored in a computer readable medium.

A server (e.g., the remote server 322 of FIGS. 3 and 12) can be distributively implemented over a network, such as a server farm, or a set of widely distributed servers or can be implemented in a single virtual device that includes multiple distributed devices that operate in coordination with one another. For example, one of the devices can control the other devices, or the devices may operate under a set of coordinated rules or protocols, or the devices may be coordinated in another fashion. The coordinated operation of the multiple distributed devices presents the appearance of operating as a single device.

In some examples, the components of the controller may be contained within a single integrated circuit package. A system of this kind, in which both a processor (e.g., the processor 318 of FIG. 3) and one or more other components (e.g., the cardiac event detector 320) are contained within a single integrated circuit package and/or fabricated as a single integrated circuit, is sometimes called a microcontroller. In some implementations, the integrated circuit package includes pins that correspond to input/output ports (e.g., that can be used to communicate signals to and from one or more of the input/output interface devices).

Although an example processing system has been described above, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification, such as storing, maintaining, and displaying artifacts can be implemented as one or more computer program products, i.e., one or more modules of computer program instructions encoded on a tangible program carrier, for example a computer-readable medium (e.g., the data storage 304 of FIG. 3), for execution by, or to control the operation of, a processing system. The computer readable medium can be a machine readable storage device, a machine readable storage substrate, a memory device, or a combination of one or more of them.

The term "system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them. In some implementations, operating systems can include a Windows based operating system, OSX, or other operating systems.

A computer program (also known as a program, software, software application, script, executable logic, or code) can be written in any form of programming language, including compiled or interpreted languages, or declarative or procedural languages, and can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM, DVD-ROM, and Blu-Ray disks. The processor and the memory can be supplemented by, or incorporated in, special purpose logic circuitry. Sometimes a server (e.g., the remote server 322) is a general purpose computer, and sometimes it is a custom-tailored special purpose electronic device, and sometimes it is a combination of these things. Implementations can include a back end component, e.g., a data server, or a middleware component, e.g., an application server, or a front end component, e.g., a client computer having a graphical user interface or a Web browser through which a user can interact with an implementation of the subject matter described is this specification, or any combination of one or more such back end, middleware, or front end components. The components of the system can be interconnected by any form or medium of digital data communication, e.g., a communication network such as the connection between the remote server 322 and the network interface 306, as shown in FIG. 3. Examples of communication networks include a local area network ("LAN") and a wide area network ("WAN"), e.g., the Internet.

Having described several aspects of at least one example of this disclosure, the examples of the methods and apparatuses discussed herein are not limited in application to the details of construction and the arrangement of components set forth in this description or illustrated in the accompanying drawings. The methods and apparatuses are capable of implementation in other examples and of being practiced or of being carried out in various ways. Examples of specific implementations are provided herein for illustrative purposes only and are not intended to be limiting. In particular, acts, elements and features discussed in connection with any one or more examples are not intended to be excluded from a similar role in any other examples. Accordingly, the foregoing description and drawings are by way of example only Also, the phraseology and terminology used herein is for the purpose of description and should not be regarded as limiting. Any references to examples or elements or acts of the systems and methods herein referred to in the singular may also embrace examples including a plurality of these elements, and any references in plural to any example or element or act herein may also embrace examples including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

What is claimed is:

1. A wearable defibrillator, comprising:
   a garment configured to be continuously worn about a torso of a patient for an extended period of time;
   one or more ECG sensing electrodes disposed in the garment, the one or more ECG sensing electrodes configured to detect an ECG signal of the patient;
   one or more therapy electrodes disposed in the garment, the one or more therapy electrodes configured to apply corrective electrical pulses to the torso of the patient;
   at least one ventilation sensor movably attached to the garment for detecting a characteristic of ventilations of a cardiopulmonary resuscitation (CPR) therapy;
   at least one chest compression sensor configured to be attached to the garment and positioned parasternally on the patient such that the at least one chest compression sensor is offset from a point at which a rescuer exerts force to deliver chest compressions;
   an output device; and
   a processor configured for
      processing information from the one or more ECG sensing electrodes, the at least one ventilation sensor, and the at least one chest compression sensor,
      determining one or more adjustments to be applied to motion data from the at least one chest compression sensor to adjust for the offset from the point at which the rescuer is exerting force to deliver chest compressions, and
      providing, to the output device, information about the CPR therapy.

2. The wearable defibrillator of claim 1, wherein the at least one chest compression sensor is configured for detecting a characteristic of chest compressions of the CPR therapy, wherein the characteristic of chest compressions of the CPR therapy comprises the motion data comprising at least one of a depth of the chest compressions and a rate of the chest compressions.

3. The wearable defibrillator of claim 2, wherein the at least one ventilation sensor and the at least one chest compression sensor is the same sensor, and wherein the same sensor comprises an accelerometer.

4. The wearable defibrillator of claim 1, wherein the at least one ventilation sensor comprises a sound sensor and the characteristic of ventilations of the CPR therapy comprises an intensity of lung sounds as detected by the sound sensor.

5. The wearable defibrillator of claim 1, comprising a memory connected to the processor, wherein the memory comprises a representation of a geometry of the patient's chest, and wherein the representation is configured to be used by the processor in determining the one or more adjustments to be applied to the motion data.

6. The wearable defibrillator of claim 5, wherein the representation of the geometry of the patient's chest is based on one or more of a) generic anthropometric data from a patient population, b) measurements of the patient, and c) a table lookup, a linear adjustment function, and a non-linear adjustment function.

7. A wearable defibrillator, comprising:
   a garment configured to be continuously worn about a torso of a patient for an extended period of time;
   one or more ECG sensing electrodes disposed in the garment, the one or more ECG sensing electrodes configured to detect an ECG signal of the patient;
   one or more therapy electrodes disposed in the garment, the one or more therapy electrodes configured to apply corrective electrical pulses to the torso of the patient;
   at least one chest compression sensor for measuring a characteristic of chest compressions of a CPR therapy, wherein the at least one chest compression sensor is attached to the garment and configured on the garment such that it is positioned parasternally on the patient such that the at least one chest compression sensor is offset from a point at which a rescuer is exerting force to deliver chest compressions;
   an output device that provides feedback to the rescuer;
   a processor configured for processing information from the one or more ECG sensing electrodes and the at least one chest compression sensor and providing, to the output device, information about the CPR therapy; and
   memory connected to the processor,
   wherein the memory comprises a representation of a geometry of the patient's chest, and
   wherein the representation is configured to be used by the processor to determine one or more adjustments to be applied to motion data from the at least one chest compression sensor to adjust for the offset from the point at which the rescuer is exerting force to deliver chest compressions.

8. The wearable defibrillator of claim 7, wherein the representation of the geometry of the patient's chest is based on one or more of a) generic anthropometric data from a patient population, b) measurements of the patient, and c) a table lookup, a linear adjustment function, and a non-linear adjustment function.

9. A wearable defibrillator, comprising:
   a garment configured to be worn about a torso of a patient;
   one or more ECG sensing electrodes disposed in the garment, the one or more ECG sensing electrodes configured to detect an ECG signal of the patient;
   one or more therapy electrodes disposed in the garment, the one or more therapy electrodes configured to apply corrective electrical pulses to the torso of the patient;
   one or more CPR sensors for detecting a characteristic of a CPR therapy, wherein the characteristic of the CPR therapy comprises motion data comprising at least one of a depth of chest compressions of the CPR therapy and a rate of the chest compressions of the CPR therapy;
   an output device; and
   a processor configured for
      processing information from the one or more ECG sensing electrodes and the one or more CPR sensors and
      providing, to the output device, information about the CPR therapy, wherein at least one of the one or more CPR sensors is movably attached to the garment, the at least one of the one or more CPR sensors configured to be positioned to the center of the patient's chest prior to initiation of the CPR therapy, wherein the at least one of the one or more CPR sensors is positioned parasternally on the patient and offset from a point at which a rescuer exerts force to deliver chest compressions, and wherein the processor is configured for determining one or more adjustments to be applied to the motion data from the at least one of the one or more CPR sensors to adjust for the offset from the point at which the rescuer is exerting force to deliver chest compressions.

10. The wearable defibrillator of claim 9, wherein the at least one of the one or more CPR sensors is configured to be repositioned from a location at the garment to the center of the patient's chest prior to initiation of the CPR therapy.

11. The wearable defibrillator of claim 9, wherein the CPR therapy comprises chest compressions and ventilations, and wherein the at least one of the one or more CPR sensors comprises a motion sensor.

12. The wearable defibrillator of claim 9, wherein the at least one of the one or more CPR sensors is stored in a compartment of the garment.

13. The wearable defibrillator of claim 12, wherein the at least one of the one or more CPR sensors is removable from the compartment and placed at the center of the patient's chest prior to initiation of the CPR therapy.

14. The wearable defibrillator of claim 12, wherein the compartment comprises a flap that is configured to fold away from the garment such that the at least one of the one or more CPR sensors is repositioned to the center of the patient's chest when the flap is folded away from the garment.

15. The wearable defibrillator of claim 9, wherein at least one of the one or more CPR sensors is positioned behind the patient when the garment is worn by the patient.

16. The wearable defibrillator of claim 15, wherein motion information from the at least one of the one or more CPR sensors positioned behind the patient is subtracted from motion information from the at least one of the one or more CPR sensors positioned to the center of the patient's chest.

17. The wearable defibrillator of claim 9, wherein the at least one of the one or more CPR sensors is configured to be repositioned to a location above the patient's xiphoid process prior to initiation of the CPR therapy.

18. The wearable defibrillator of claim 9, wherein at least one of the one or more CPR sensors is configured to communicate wirelessly with the processor.

19. The wearable defibrillator of claim 9, wherein at least one of the one or more CPR sensors is integrated with the one or more therapy electrodes.

20. The wearable defibrillator of claim 9, wherein at least one of the one or more CPR sensors is discrete from the one or more ECG sensing electrodes and the one or more therapy electrodes.

21. The wearable defibrillator of claim 9, wherein the output device comprises at least one of an audio output device, a display disposed on the wearable defibrillator, and a wireless transceiver for communicating with an external device having a display.

22. The wearable defibrillator of claim 21, wherein the audio output device is configured to provide rhythmic audio indicative of a target rate of chest compressions for the CPR therapy based on the information about the CPR therapy.

23. The wearable defibrillator of claim 21, wherein the audio output device is configured to provide one or more verbal commands to a user administering the CPR therapy to the patient based on the information about the CPR therapy.

24. The wearable defibrillator of claim 23, wherein the one or more verbal commands are related to one or both of the rate of chest compressions and the depth of chest compressions of the CPR therapy being administered to the patient.

25. The wearable defibrillator of claim 21, wherein at least one of the display disposed on the wearable defibrillator and the display of the external device is configured to present, based on the information about the CPR therapy, one or both of the rate of chest compressions and the depth of chest compressions of the CPR therapy being administered to the patient.

26. The wearable defibrillator of claim 21, wherein at least one of the display disposed on the wearable defibrillator and the display of the external device is configured to present, based on the information about the CPR therapy, one or more instructions to a user administering the CPR therapy to the patient.

27. The wearable defibrillator of claim 26, wherein the one or more instructions are related to one or both of the rate of chest compressions and the depth of chest compressions of the CPR therapy being administered to the patient.

28. The wearable defibrillator of claim 9, wherein the garment comprises a pressure-sensitive fabric.

29. The wearable defibrillator of claim 9, comprising a memory connected to the processor, wherein the memory comprises a representation of a geometry of the patient's chest, and wherein the representation is configured to be used by the processor in determining the one or more adjustments to be applied to the motion data.

30. The wearable defibrillator of claim 29, wherein the representation of the geometry of the patient's chest is based on one or more of a) generic anthropometric data from a patient population, b) measurements of the patient, and c) a table lookup, a linear adjustment function, and a non-linear adjustment function.

* * * * *

UNITED STATES PATENT AND TRADEMARK OFFICE
CERTIFICATE OF CORRECTION

PATENT NO. : 10,561,575 B2
APPLICATION NO. : 15/463117
DATED : February 18, 2020
INVENTOR(S) : Gary A. Freeman et al.

Page 1 of 1

It is certified that error appears in the above-identified patent and that said Letters Patent is hereby corrected as shown below:

In the Specification

Column 12, Line 44, delete "ventrical", insert -- ventricular --
Column 30, Line 20, delete the second instance of "chest", insert -- Chest --
Column 40, Line 67, delete "only", insert -- only. --

Signed and Sealed this
Seventh Day of April, 2020

Andrei Iancu
*Director of the United States Patent and Trademark Office*